United States Patent [19]

Lichtenstein

[11] Patent Number: 4,464,172

[45] Date of Patent: Aug. 7, 1984

[54] COMPUTER-CONTROL MEDICAL CARE SYSTEM

[76] Inventor: Eric S. Lichtenstein, 420 Taconic Rd., Greenwich, Conn. 06830

[21] Appl. No.: 222,772

[22] Filed: Jan. 6, 1981

Related U.S. Application Data

[60] Division of Ser. No. 34,539, Apr. 30, 1979, Pat. No. 4,379,983, which is a continuation-in-part of Ser. No. 915,472, Jun. 14, 1978, abandoned, which is a continuation of Ser. No. 670,608, Mar. 26, 1976, abandoned, which is a continuation-in-part of Ser. No. 625,738, Oct. 24, 1975, abandoned, which is a division of Ser. No. 494,006, Jul. 31, 1974, Pat. No. 3,946,731, which is a continuation-in-part of Ser. No. 3,912,455, Oct. 14, 1975, , which is a continuation-in-part of Ser. No. 108,118, Jan. 20, 1971, Pat. No. 3,774,762, and Ser. No. 157,942, Jun. 29, 1971, abandoned.

[51] Int. Cl.$^3$ .............................................. A61M 1/03
[52] U.S. Cl. ............................. 604/65; 128/DIG. 13
[58] Field of Search ............................... 128/765–766, 128/DIG. 3; 604/66; 210/87–90

[56] References Cited

U.S. PATENT DOCUMENTS

| | | | |
|---|---|---|---|
| 3,043,303 | 7/1962 | Still | 604/66 |
| 3,319,623 | 5/1967 | London | 604/66 |
| 3,946,731 | 3/1976 | Lichtenstein | 604/66 |

*Primary Examiner*—Kyle L. Howell
*Assistant Examiner*—Francis J. Jaworski
*Attorney, Agent, or Firm*—Blum Kaplan Friedman Silberman & Beran

[57] ABSTRACT

A computer-controlled medical care system for use in the treatment and diagnosis of patients provides for either automatic or manual control of a wide variety of medical procedures including diagnostic procedures. The system accepts modular vessel structures, each type of structure being adapted for carrying out a specific procedure and matching programs for carrying out the specific procedures. A microcomputer accepts a program which may be designed to fit the needs of a specific patient and which must watch the modular vessel structure. The microcomputer monitors the progress of the process and the physiological status of the patient and provides for the taking of appropriate steps should difficulties be encountered in carrying out the procedure. The system can also be programmed to analyze a fluid taken from an individual, to treat the fluid and return same to the individual and to schedule the infusion of appropriate medications.

Embodiments of the system provide for carrying out only a limited group of procedures where a full-range system is undesirable either because unnecessary or uneconomic.

Modular vessel structures are keyed to specific programs, thereby preventing operator errors and increasing the reliability of the system.

13 Claims, 15 Drawing Figures

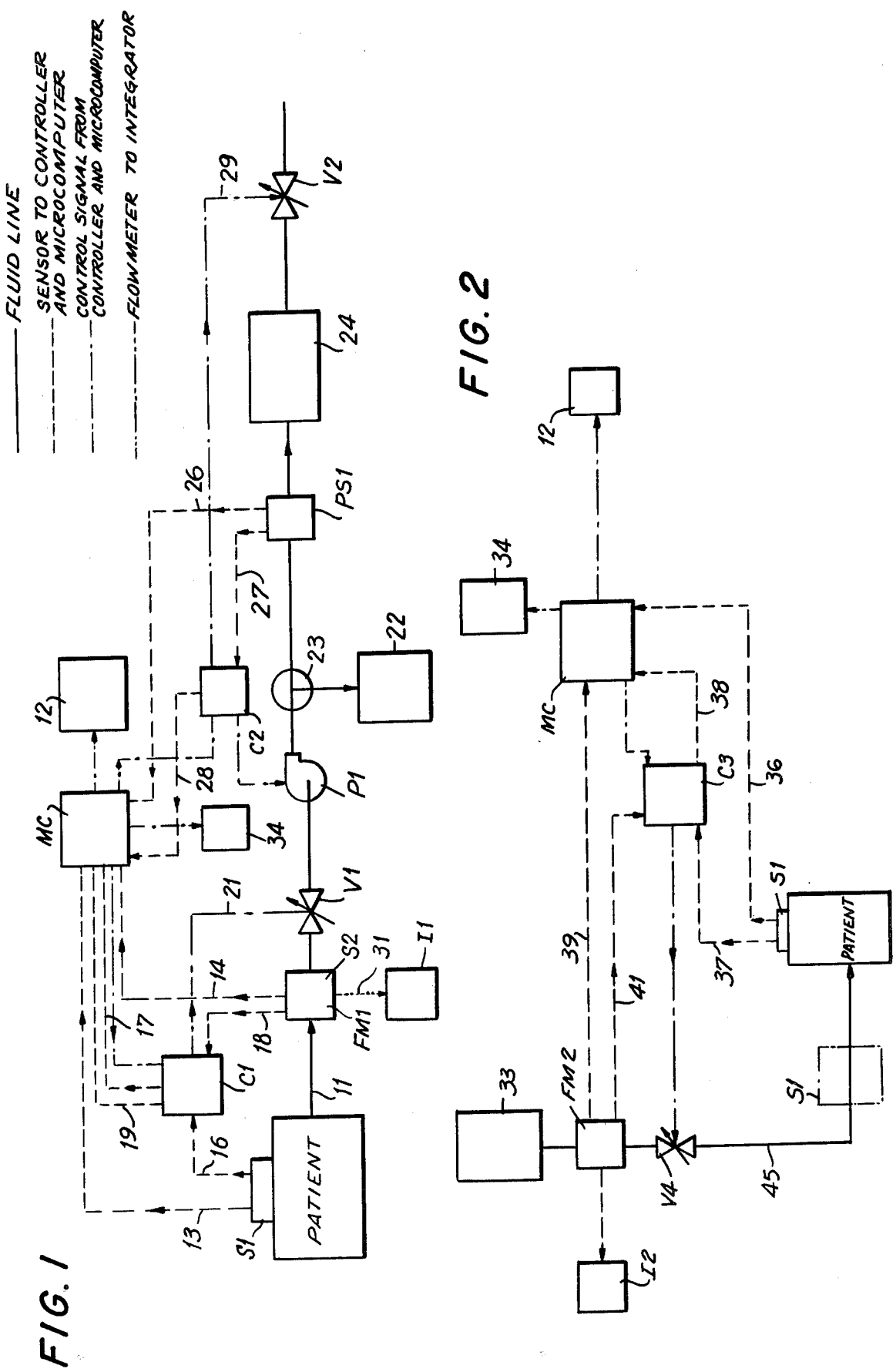

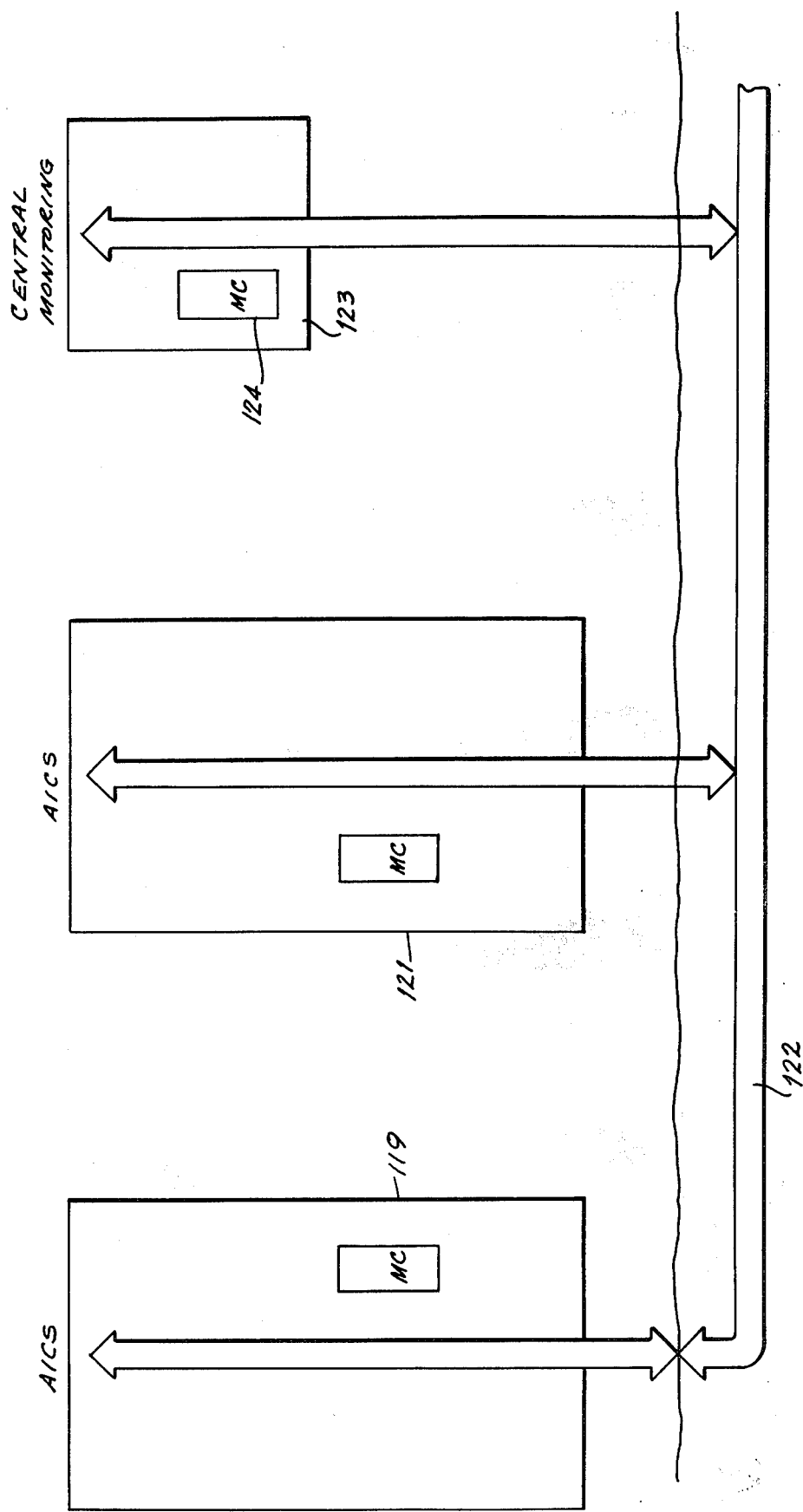

FIG.8A
FIG.8B
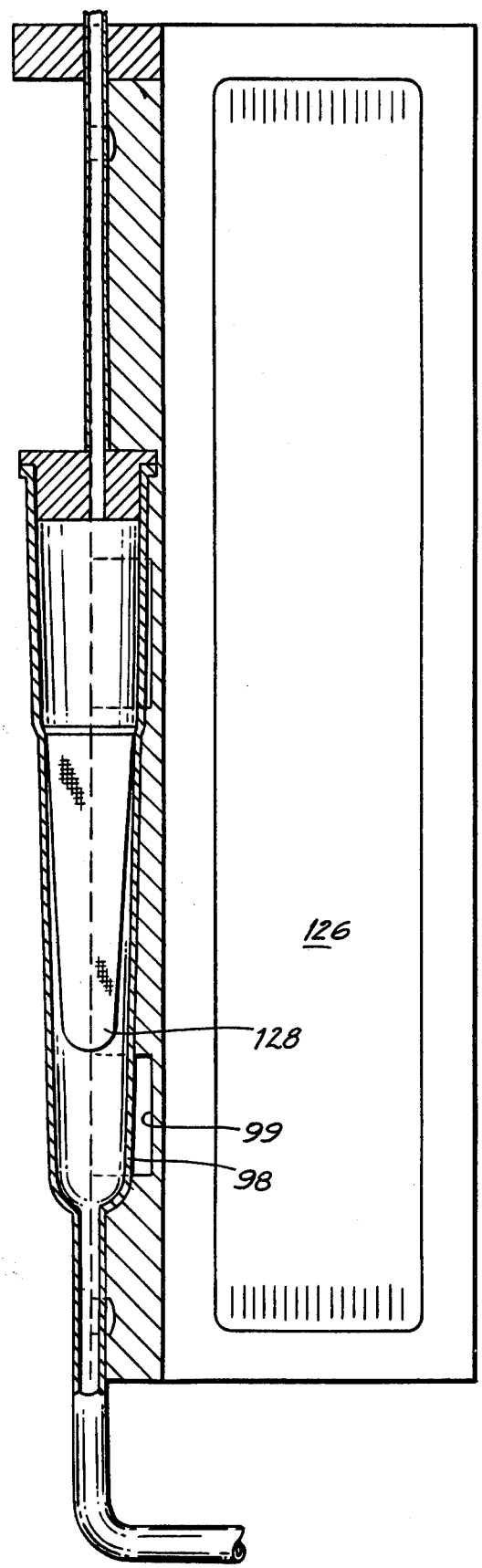
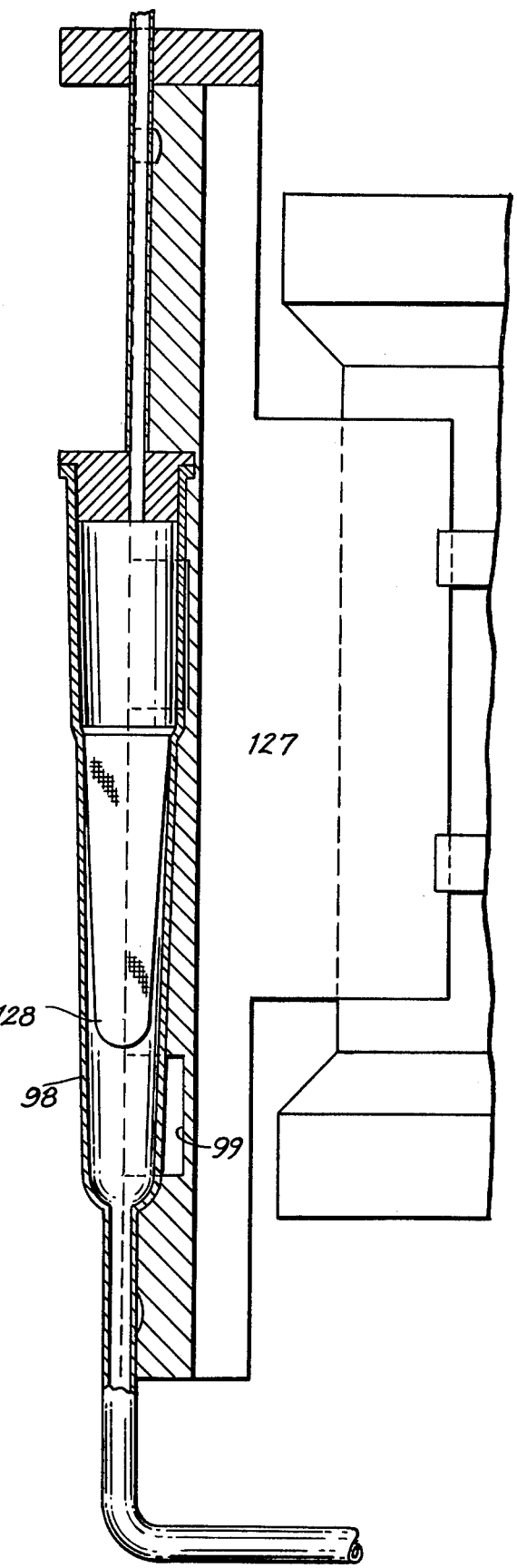

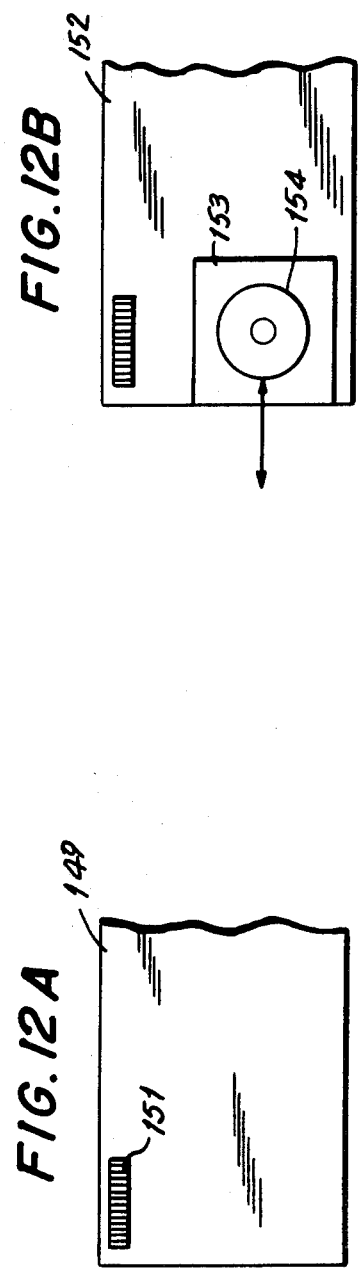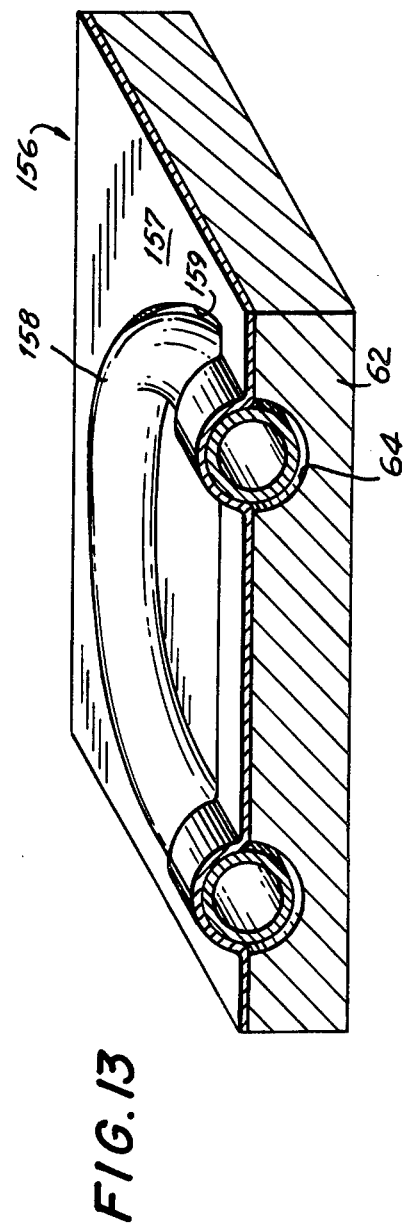

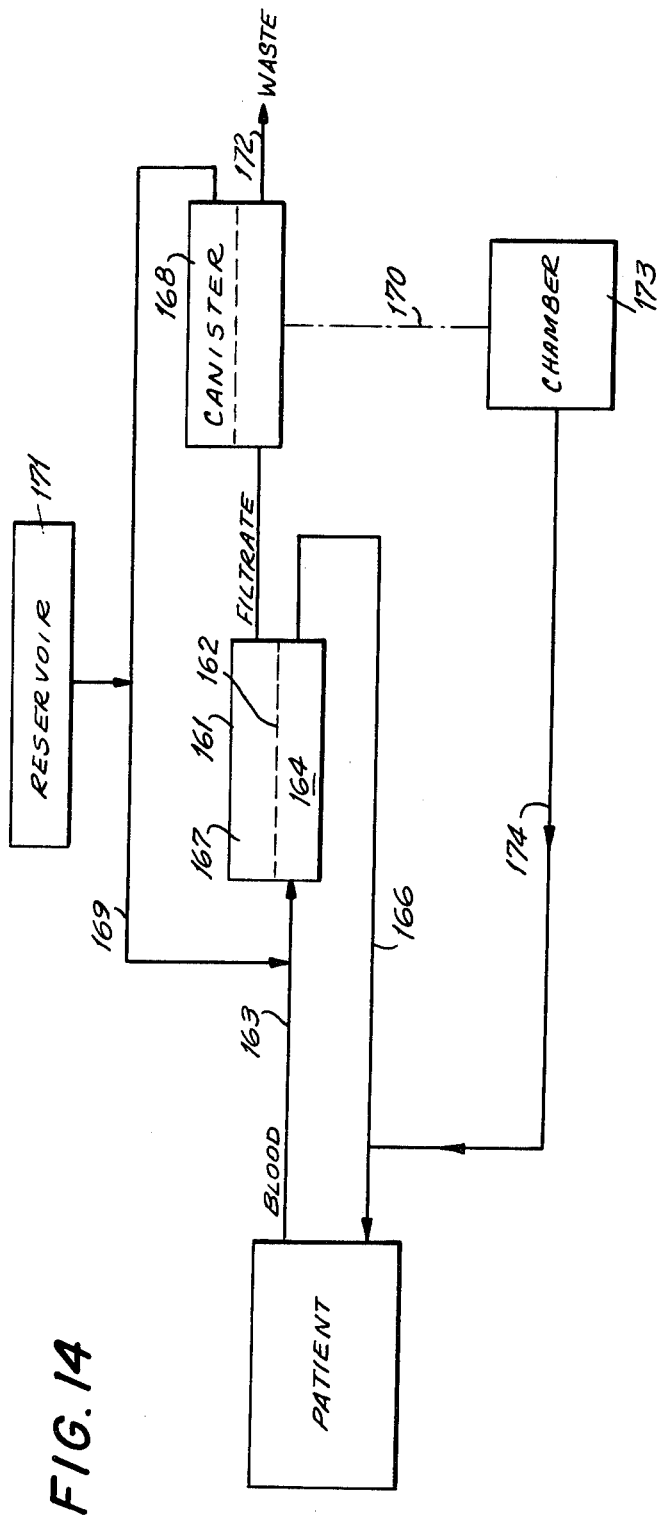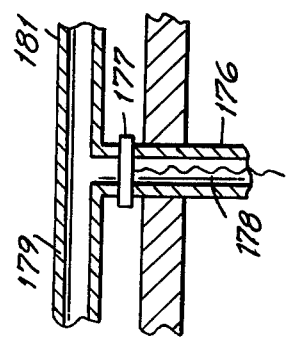
FIG. 14
FIG. 15

COMPUTER-CONTROL MEDICAL CARE SYSTEM

CROSS-REFERENCE TO RELATED APPLICATIONS AND PATENTS

This is a division of application U.S. Ser. No. 34,539, filed Apr. 30, 1979 now U.S. Pat. No. 4,379,983, which is a continuation-in-part of U.S. Ser. No. 915,472, filed June 14, 1978, now abandoned, itself being a Continuation of U.S. Ser. No. 670,608, filed Mar. 26, 1976 now abandoned; itself a continuation-in-part application of U.S. Ser. No. 625,738, filed Oct. 24, 1975 now abandoned; itself a Divisional application of U.S. Ser. No. 494,006, filed July 31, 1974 and which issued as U.S. Pat. No. 3,946,731, itself being a continuation-in-part application of U.S. Pat. No. 3,912,455, issued Oct. 14, 1975, said patent being a continuation-in-part application of U.S. Ser. No. 108,118, filed Jan. 20, 1971 and U.S. Ser. No. 157,942, filed June 29, 1971 and now abandoned. Ser. No. 108,118 issued as U.S. Pat. No. 3,774,762 on Nov. 27, 1973.

BACKGROUND OF THE INVENTION

In previously co-pending application Ser. No. 494,006, now issued as U.S. Pat. No. 3,946,731, titled "APPARATUS FOR EXTRACORPOREAL TREATMENT OF BLOOD", (said patent being incorporated herein by reference as if fully presented as are also my U.S. Pat. Nos. 3,912,455 and 3,774,762) the apparatus disclosed was directed to withdrawal of blood from a patient, extracorporeal treatment of blood for the purpose of altering its physiologic characteristics and reinfusion of the treated blood to provide a patient with substitute or improved bodily functions. As described in patent '731, such extracorporeal circulation requires control of a substantial number of variables, some of the variables being so critical that failure to control them appropriately can result in death of the patient. Also, the number of variables which must be controlled can be sufficiently large so that it can be almost impossible for an attendant to monitor the variables, make decisions as to what adjustments are necessary and then to carry them out, this difficulty rendering it desirable that monitoring and a major portion of the decision-making, at least, be carried out automatically.

It is now seen that apparatus such as described in '731 can be used for a variety of purposes some of which require only portions of said apparatus rather than the entire apparatus with substantial benefit to the patient through improved monitoring and control of the processes carried out by said portions of the apparatus, thereby increasing the reliability of the procedure and reducing the cost of same.

The variables which must be monitored fall into a hierarchy of importance which requires that the most crucially-important variables associated with the safety of the patient can override those of lesser importance. Accordingly, automatic compensation for variation in those parameters of lesser importance can be gauged by response to those parameters designated to be of greater significance to either the patient's safety, primarily, or, secondarily to continuation of the treatment procedure.

While automatic control of procedures has been available for many years, the instrumentation used has been based on analogue techniques. Thus, in proportional control, a controller would be used for adjusting a valve so that the flow through the valve would be proportional to the difference between a measured flow rate and a flow-rate corresponding to a set-point. Initially, the relationship between the valve opening and the deviation from the set-point was based on a mechanical device or an electromechanical device. In a later stage of development, the control method was electronically operated, but was still based on analogue signals throughout. Recently, however, computers have been developed which, in cooperation with sensors providing analogue outputs and ancillary analogue-to-digital and digital-to analogue converters operate completely in a digital mode. Such computers can be programmed for providing control which is far more accurate and reliable than has previously been possible. Moreover, these digital computers have been progressively miniaturized and the cost thereof has been decreased to such an extent that microcomputers dedicated to a specific purpose have become feasible both from the standpoint of carrying out the dedicated task and from the standpoint of cost. Moreover, such microcomputers can be programmed for carrying out a wide variety of procedures and even for modifying the procedures to take account for the needs of specific patients.

As is evident, such computers can readily be designed for receiving signals from and for participating in the control of a patient-care system where the range of procedures to be carried out by the system is limited to a single group or extends over a wide range encompassing those groups under the term "intensive care". Since the computers can be adapted to cooperate with the hardware of the system either for carrying out control operations automatically or for indicating control steps to be taken by an attendant, systems can be readily designed with respect to the specific needs of an institution or of an individual. It can thus be seen that with the advent of the minicomputer, it becomes possible to effect a substantial reduction in the cost of caring for patients and to increase the reliability of the care extended to patients but a design is needed which can readily be matched to a wide variety of needs.

SUMMARY OF THE INVENTION

The present invention is an improved apparatus for monitoring and control of medical, diagnostic and therapeutic procedures involving the withdrawal, infusion or extracorporeal circulation of fluid from or to a patient. Such procedures are called for in a variety of medical conditions. The invention includes hardware for carrying out the specific steps of a given procedure, software for control of the hardware in carrying out the steps and modular vessel structure, hereinafter referred to as modules, for cooperation with the remainder of the system in carrying out said procedures.

Generally speaking, the computer-controlled medical care system of the present invention comprises a computer means for receiving any of a plurality of programs, a support for holding any of at least two different types of modules where each type of module includes at least one duct connectible with an individual, fluid transfer means such as a pump or a gravity feed device for transferring fluid through a duct in said module at a rate corresponding to a selective program, at least one sensor for sensing the rate of transfer of fluid within the module, the sensor being connected with the computer and indicator means connected with the computer for indicating the status of the procedure underway relative to the selected program and for indicating any adjustment necessary for establishing correspondence between the progress of the procedure and the selected program. More generally, the sensor may be disposed for measuring a variable relative to the fluid within the module or relevant to the status of the patient.

The module is generally, but not always, disposable. It may be made of plastic sheet formed into plastic tubing or of conventional tubing, it being necessary that the plastic tubing or the conventional tubing be of a medically-acceptable material. The module is formed in a fixed pattern to provide a definite array of flow paths corresponding to the procedure for which it is designed. It is generally considered disposable in order to decrease the possibility of patient-to-patient or patient-to-staff contamination.

The hardware of the system which includes valves and pumps can be operated by the microcomputer in accordance with a selected program either automatically or by means of an attendant through instructions displayed on appropriate equipment.

In the embodiment of widest applicability, the system can take fluid from an individual, infuse fluid to an individual and can process fluid. In this last operation, fluid may be taken from an individual as in hemodialysis, treated and then returned to the individual. Alternatively, fluid may be taken from an individual, processed, optionally stored and then either transfused to another individual or reinfused to the same individual. Fluid taken from an individual may be subjected by the system to analysis as the basis for diagnosis after which the microcomputer in cooperation with the selected program can schedule medication for infusion.

In another embodiment of the invention, systems are designed for carrying out a specific group of procedures such as only taking fluid, examples of such procedures being taking blood for storage, taking blood for separation into components which can then be sent to different destinations and taking fluid for chemical and biochemical analysis.

In yet another embodiment of the invention, the system can be designed for infusion of fluids only. The procedures in this group encompass infusion of IV fluids and periodic infusion of medication with scheduling both as to time and quantity.

A particularly significant feature of the present invention is a module which can be keyed to a specific procedure. This feature makes it possible to insure that a program inserted into the microcomputer for carrying out a specific procedure is matched to the module for carrying out the same procedure.

Accordingly, an object of the present invention is an apparatus for transferring body fluids including blood to or from a patient, the apparatus incorporating a microcomputer which is programmable.

Another object of the present invention is an apparatus for transferring body fluid from a patient where the body fluid is to be subjected to automatic analysis in said apparatus.

A further object of the present invention is an apparatus for injecting fluids into a patient under the control of a microcomputer where infusion fluids may be transferred for the purpose of alimentation or medication.

A significant object of the present invention is an apparatus for extracorporeal circulation and treatment of body fluids taken from and returned to a patient.

Yet another object of the present invention is an apparatus for hemodialysis incorporating a programmable microcomputer and sensors for sensing the physiological status of the patient and the rate of blood flow, the microcomputer being connected with a display means for indicating any adjustments in the system which need be made.

An important object of the present invention is a hemodialysis system wherein a programmable microcomputer receives signals from various sensors as to the physiological status of the patient, the rate of flow of blood, the rate of flow of dialysate and the pressure difference across the semipermeable membrane of a dialysis canister, the operation of the dialysis membrane support system being programmable to take account of a particular procedure and schedule to be followed for a specific patient, the physiological status of the patient and the stage of the process under way, the microcomputer adjusting set points of the various subordinate controllers in accordance with the above variables to protect the patient and maintain the process under optimum conditions.

A desired object of the present invention is a hemodialysis system incorporating a second membrane support for recovering at least portions of the solution transferred from the blood by ultrafiltration, the solution being recoverable from the dialysate, taking the solution and transferring it back to the input side of the dialysis canister in combination with dialysate concentrate.

A particular object of the present invention is a module which is keyed to insure correspondence between the procedure for which the module is designed and the program inserted into the microcomputer for carrying out the procedure.

Yet another object of the present invention is a method of operating an apparatus for transferring fluid from or to a patient which makes it possible to carry out any of a variety of medical procedures including both diagnostic and therapeutic procedures.

Still other objects and advantages of the invention will in part be obvious and will in part be apparent from the specification.

The invention accordingly comprises the several steps and the relation of one or more of such steps with respect to each of the others, and the apparatus embodying features of construction, combination of elements and arrangement of parts which are adapted to effect such steps, all as exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 1 is an apparatus for taking fluid from a patient where the fluid is to be subjected to processing or analysis;

FIG. 2 is an apparatus for transferring fluid to a patient; and

FIG. 7B shows schematically two systems in accordance with the present invention connected with a central bus communicating with a central monitoring unit where the two embodiments may differ from each other or be the same and may be functioning in connection with different patients or with the same patient;

FIG. 8A is a sectional view of one portion of a flat plate hemodialyzer;

FIG. 8B is a sectional view of one portion of a tubular membrane hemodialyzer;

FIGS. 12A and 12B illustrates coding of a module;

FIG. 13 illustrates how a module is held in a fixed pattern;

FIG. 14 illustrates an embodiment for carrying out hemofiltration and plasmapheresis; and FIG. 15 illustrates a reusable pressure sensor.

DESCRIPTION OF THE PREFERRED EMBODIMENTS

Figure 3:
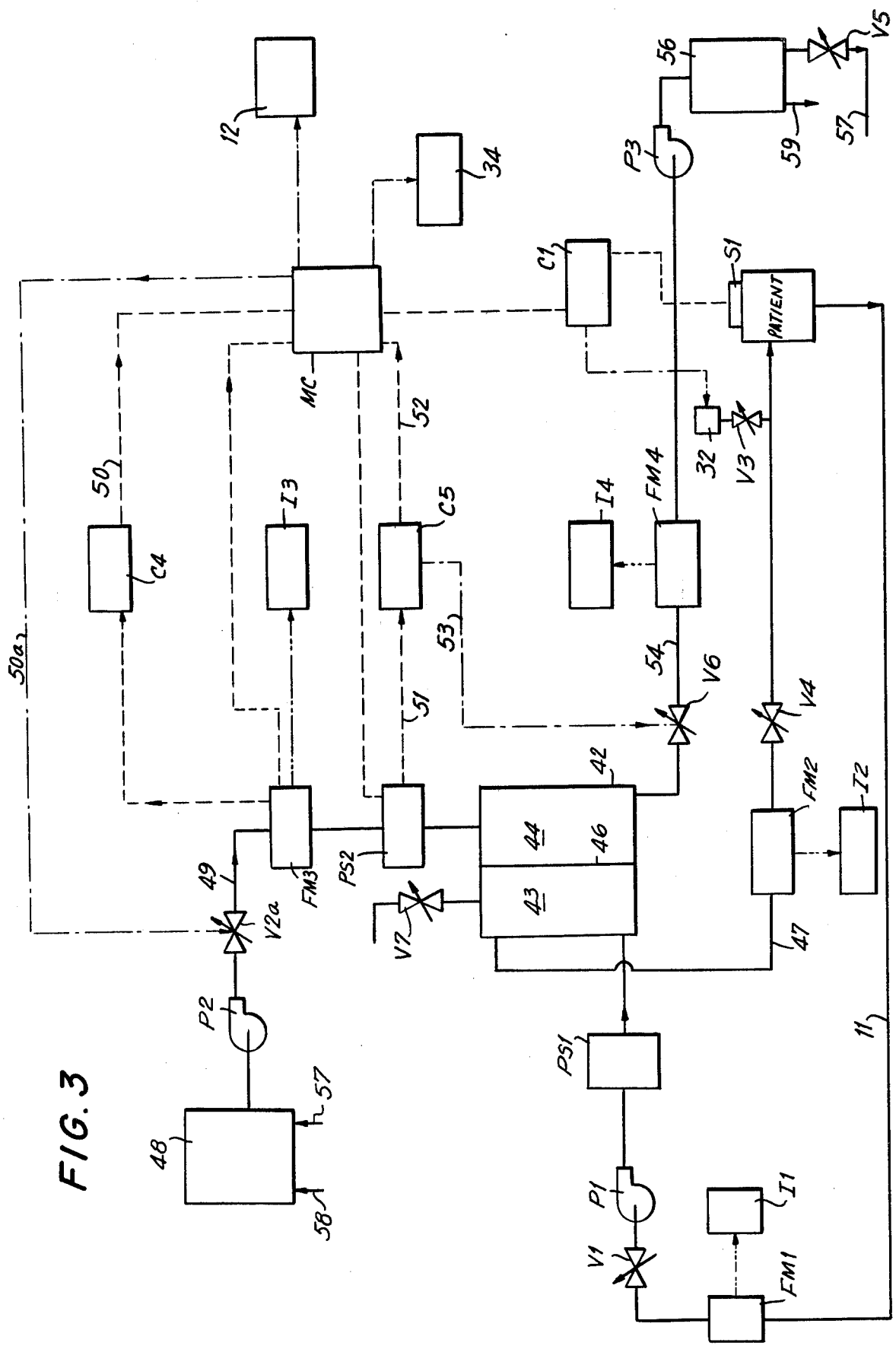
FIG. 3 is an apparatus for extracorporeal treatment of fluid.

The computer-controlled medical care system of the present invention can be designed for carrying out a wide range of treatments of patients. It can be constructed in a variety of embodiments ranging from those which can carry out only a limited number of procedures such as the infusion of physiologic fluids to embodiments which can carry out virtually any type of procedure including those necessary for treatment of profound physiologic disturbances such as those which may be classified as shock syndromes. Shock conditions can be associated with a variety of etiologies due to loss of blood or physiologic fluids, as for example in surgery, post-surgical recovery, trauma, hemorrhage, gastrointestinal obstruction, diabetes insipidus, fluid and electrolyte imbalance, as in diabetes mellitus and burns. Adrenal and renal insufficiency are examples of other conditions requiring intensive monitoring and precise control of therapy that are amenable to care by means of the system of the present invention.

Other types of procedures which can be carried out with appropriate monitoring are hemodialysis, ultrafiltration, hemofiltration, hemoperfusion, medical drainage and irrigation procedures including monitoring of urinary output, gastro-intestinal tube suction, and biliary or wound drainage by way of catheter either with or without continuous irrigation. The use of irrigation for continuous urinary bladder drainage by catheter to reduce the incidence of infection is a standard procedure, but conventional techniques preclude simultaneous or concomitant accurate assessment of urine output. Bladder irrigation has not, therefore, been used in shock patients despite the fact that the output of urine provides a good indication of the adequacy of tissue perfusion with blood. Monitoring the difference between inflow of irrigation fluid and outflow, as with the monitoring and control of dialysate to measure ultrafiltration shown in my earlier patents will allow either irrigation and urine measurement or just urine output monitoring by the system, with inflow set at zero and output pumping controlled by pressure.

The system can be adapted to various specialized monitoring requirements, as, for example, monitoring the pulmonary capillary wedge pressure indicative of the function of the left side of the heart by the use of an arterial blood pressure line or with modification of the module (system) to specify in programming the use of one of the infusion systems pressure transducers. Provision may be made in the hardware to connect two or more parts of the apparatus electronically under a single microcomputer or under the control of cooperating microcomputers to provide a plurality of functions as required. This will be discussed further in the description of the electronic system architecture, utilizing the "Data Bus".

A wide variety of sensors can be used effectively in the system shown herein, the system itself including a variety of modular vessel structures and a matching support within the system for cooperating with the modules. The modules themselves may carry various sensors such as disposable electrodes for monitoring electrocardiographic data from the patient. The module may also include portions of sensors, such as the disposable diaphragm component of a pressure transducer, or flow-meter impeller units. A portion of the apparatus, hereinafter termed the "interface", is designed for supporting the module and cooperating directly therewith. The interface may include one or more sensors for determining pressure and rate of fluid flow within ducts and chambers in the module. Also included may be sensors for invasive or noninvasive determination of intravascular pressures within a patient connected with a module and arrangements for gravity flow or pumped flow of fluid between a module and a patient or within the module.

A key feature of the system is a microcomputer which is programmable for carrying out specific procedures. Control of a procedure involves monitoring variables such as pressure and rate of flow of fluids through the module and between the module and a patient, monitoring the physiologic status of the patient, determining whether the procedure must be modified in accordance with the stage of the procedure and/or the condition of the specific patient and then controlling the procedure. Control of the procedure may be carried out either by an attendant on the basis of indications generated by the microcomputer in an appropriate display or automatically. For effecting adjustment of the procedure, adjustable valves and controllable-rate pumping are provided by the system. The adjustment of the various flow rates can be effected either manually by an operator or automatically where control means are provided. Needless to say, the automatic control means may be either internal to or external to the microcomputer, but in either case, the automatic control means may be regarded as part of the microcomputer.

Where the physiologic disturbance for which the patient must be treated is critical in nature, it may become extremely difficult, and economically prohibitive for attendants, no mattter how highly skilled, to monitor parameters and to determine what steps must be taken and then to take the appropriate steps in modifying the procedure which may be underway. For example, where a patient is in shock, in addition to basic monitoring of blood pressure, urine output, and pulse rate, etiologic parameters such as volume of fluid lost or cardiac electrical activity pattern may be essential parameters of physiologic functions which must be considered in addition to other variables. These parameters, sensed by appropriate "Module-Interface" construction and microcomputer programming can easily be integrated into the programmed therapeutic algorithm. Techniques for calculating heart rate from the peaks of electrical activity are standard monitoring unit functions, and rate calculations are part of the various computer ECG interpretation programs. With the use of such ECG interpretation programs to indicate the types of arrhythmia, the medical care system can be designed and programmed to treat automatically such life-threatening conditions as well as to give an alarm signal should sensors in the system indicate that a condition has arisen with which the system cannot cope.

The system of the present invention is designed for grouping the signals coming to the microcomputer from the various sensors into a hierarchy on the basis of the criticality of the information. Thus, where the program calls for holding the flow of a fluid such as an infusion fluid within a certain range, should the rate of fluid flow have a value outside this range, then the microcomputer will signal the appropriate adjustment. Should the rate of fluid flow remain outside the appropriate range for longer than a selected period, the microcomputer will then generate an alarm signal and indicate the appropriate steps to be taken to protect the patient, such an appropriate step being, for instance, the shutting of a valve connecting the patient with the module so as to stop the flow of fluid from the module to the patient. On the other hand, should the signal be one which indicates that the life of the patient is in jeopardy such a signal being a precipitous drop in blood pressure, then the microcomputer is designed to generate the alarm signal immediately as well as to take the appropriate steps without delay to protect the patient.

In general, the system is designed to be fail-safe in that a positive signal must be supplied to the microcomputer from an appropriate sensor in order to prevent the generation of an alarm signal and the taking of protective steps. Such a positive signal might be the continuation of the heart-beat of the patient, indication that fluid flow is continuing and that passages are open, the pressure is within specified limits, and the like. The monitoring of fluid temperature, pressure, air-fluid level in a debubbler as well as the condition of the patient all contribute to safe therapy.

The apparatus may be adapted to the monitoring simultaneously of arterial and pulmonary capillary wedge pressures. These can be used to optimize the treatment of cardiogenic shock by precise computer control of vasodilator and cardiotonic drugs to reduce myocardial work without sacrificing tissue perfusion. This form of therapy is currently available, but its cost is prohibitive. The present system will make such complex care readily, and cost-effectively available.

Further applications of the system utilizing appropriately constructed modules and such additional sensors as may be necessary, are the withdrawal of blood samples for analysis, chemical or by substance-specific electrodes, and computer-controlled drug infusions. Assay of glucose and of electrolyte and arterial blood gases can, for example, be used to monitor and treat diabetes, including as will be described below, multiple hormone and drug administration in complex patterns.

Equipment which can be readily coupled together into a microcomputer for carrying out the functions and controlling the processes to be described herein is widely available from a number of sources. While such a microcomputer can be based on analogue circuitry, digital information processing units are now more widely used for control operations and examples of such equipment will be presented. For convenience and to avoid a multiplicity of listings the products of Digital Equipment Corp. (DEC) of Maynard, Mass. will be specified to exemplify how the microcomputer of the present invention is to be assembled, but the invention is not to be considered as restricted to DEC components or to digital information processing components. Moreover, products of other manufacturers may be used in combination with DEC components.

The microcomputer can be assembled from control processing unit (CPU) catalogued as PDP 11/03, dual RVX11 floppy disc memory and VT52 cathode ray terminal (CRT). These microcomputer constituents are standard items which are so constructed that they can be joined together by plug and socket connections.

The microcomputer is programmable to fit the specific procedure to be carried out as well as the specific patient. Moreover, signals from sensors sensitive to variables such as the physiological status of the patient, the rate of flow of fluid and pressure of fluid under transfer after conversion to digital form can be transmitted directly to the microcomputer which, optionally, is connected to a display means for indicating the sensed parameters and/or any needed adjustments in the operating conditions to maintain the procedure on schedule while keeping the physiological status of the patient within predetermined limits.

An example of a sensor which may be joined with the DEC computer components is the transducer manufactured by Gould-Statham Instruments, Inc. of Hato Rey, Puerto Rico. The P-23 Series of such medical transducers can be used for measuring of arterial or venous pressure as well as intracranial pressure and muscular tension. A large number of medical transducers which may be plugged into the master controller is listed in Medical Electronic News of March 1975, page 6. The list includes devices for measuring blood pressure, blood flow, pulse rate, blood velocity and skin resistance, among other variables.

The signals produced by sensors are generally in analogue form. These signals are converted to digital form before transmission from the sensor to the microcomputer. Additional signal conditioning, especially for the 0–10 V range is provided by the DEC components LPSAG, PLSAD-NP and LPSDR. These also provide peripheral memory and program-controlled relays which allow operation of motors and other analogue devices such as areemployed in the valves, pumps and safety devices to be described. The LPS devices include program-controlled, normally-open relays which can be used to operate fail-safe devices for isolating the patient, that is, terminating the flow of blood or other fluid from or to the patient and for triggering an alarm signal.

Signals from the sensors, after conversion to digital form, go to appropriate digital controllers, for comparison with a set point and limits on either side of the set point defining a desired operating range and with the program of the microcomputer, the controllers being connected to appropriate control means for maintaining the variables within the desired limits. Since the set point, usually, must change with time, that is, with the progress of the procedure and with the condition of the patient, the microcomputer in accordance with the program which has been set into it then adjusts the set points of the various subordinate controllers to maintain the patient's physiological status within acceptable limits and to make any necessary adjustments in the set point to correspond to the stage of the treatment. Alternatively, the microcomputer is programmed for displaying the adjustments in a procedure under way to be made by an attendant.

A suitable controller is the DEC industrial Controller System (ICS) which operates under the control of the (Central Processing Unit) program as an input/output device capable of integrating both analogue and digital inputs and driving both digital and analogue outputs, i.e., controlling both digital and analogue devices. As a process controller, it is designed for operation of both AC and DC slave systems such as can be used to drive solenoid valves electric motors with stepping speed controls while constantly monitoring the functions controlled through these slave systems.

As is the case with all three FIGS. 1–3, FIG. 1 illustrates an arrangement of the apparatus in which signals are received from various sensors by microcomputer, hereinafter termed MC, for processing according to a program specific to the process under way in the apparatus and specific to the patient. The MC then determines what adjustments, if any, are to be made in the process and then displays the required adjustments in an appropriate display means.

Alternatively, the signals from the various sensors may go to controllers which are subordinate to the MC in that the set points of the various controllers are adjustable by the MC. The signals are then sent to the MC for processing as before. However, instead of using any of the aforenoted display means, the changes called for by the MC are returned to the various subordinate controllers, and these in turn carry out the necessary adjustments automatically. In such case, one or more subordinate controllers act as, and are synonymous with, the display means of the first embodiment. It should be noted that the various controllers as well as MC may be regarded as elements of a single on-line computer-control system. This concept applies to all of the other embodiments shown in the various Figures and described herein.

Returning now to FIG. 1, sensor, S1, determines the physiologic status of the patient in one or more ways. Pertinent are the blood pressure of the patient, the pulse rate, the concentration of one or more ions as determined by ion-specific electrodes and the concentration of various compounds in the blood as determined by appropriate automatic means. The blood pressure may be determined at an intravascular access point which may be arterial, venous or a derivative of these as by use of a surgically created A-V fistula, the value of the measured blood pressure then depending on the site and anatomy of vascular access. Also, the blood pressure may be determined non-invasively and periodically by an external fixture. It is difficult and expensive to position a sensor at an intravascular point. Accordingly, although S1 is shown as being located at the patient, when sensor function can be external as where S1 is designed to measure blood pressure, it is preferably placed in fluid-withdrawal line 11 through which the fluid flows on its way to an analytical section or a fluid processing section. The pressure in the line corresponds to that at the access point when the rate of flow is sufficiently low.

Where control of the operating conditions of the apparatus is to be carried out by an attendant on the basis of information supplied by display means 12, the signal from S1 is transferred directly through line 13 to MC. Also, flow meter FM1 has therein a sensor S2 which transmits a signal through line 14. Pump P1 provides flow of fluid through line 11. In a preferred embodiment, pump P1 generates a pulsating flow in which there is a short interval or instant during which the flow is zero. Under such circumstances, the blood pressure in line 11 will be equal to that in the vasculature of the patient and will not include error due to a pressure drop in the system caused by flow therethrough. However, an additional connection with the vascular system of the patient may be made for measuring a blood pressure relevant to a specific procedure directly.

The MC processes the information received from sensors S1, S2, etc., and determined whether any adjustment need be made with respect to the rate of taking fluid from the patient. Should any adjustment be necessary, the appropriate adjustment will be shown in display means 12. Adjustment of the flow rate can be made by means of control valve V1 or pump P1.

Where one or more subordinate controllers are provided, the signal from sensor S1 is transmitted through line 16 to controller C1, and from controller C1 through line 17 to the MC. The MC then determines whether the signal from S1 lies within the acceptable range set into controller C1 by the MC on the basis of a predetermined program, specific to the patient and to the process to be carried out. Similarly, sensor S2 transmits a signal through line 18 to controller C1 and thence through line 19 to MC.

Controller C1 then automatically adjusts the flow rate through conduit 11. As shown in FIG. 1, the adjustment is made by a signal sent over line 21 to control the valve V1. As aforenoted, the flow rate could also be controlled by adjustment of pump P1.

Attention is called to the fact that conduits in the Figures through which fluid flows are shown as solid lines, signals to a controller or to the MC are shown as dashed lines and control signals from the MC or a subordinate controller are shown in dot-dashed lines.

As is evident, signals from S1 could be sent directly to the MC while the signals from S2 could be transmitted to controller C1 and thence to MC for processing by the MC. Moreover, if both signals from S1 and S2 are first sent to the controller C1, a composite signal could be sent to MC. Such modifications of the apparatus are well within the skill of one having conventional knowledge of control art.

Where the apparatus is to be used only for the analysis of fluid taken from a patient, the fluid is taken directly to analytical section 22. In FIG. 1, the apparatus is shown as being suitable for use either for analysis of body fluid or for processing of the fluid. Consequently, a three-way valve means 23 is disposed in conduit 11. When appropriately oriented, the valve means 23 directs fluid for analysis to analytical section 22. Alternatively, stop cock 23 can be turned to direct fluid toward fluid processing section 24. On occasion, in the processing of fluid, it is necessary to control the pressure at a specific value or through a course of values in accordance with a preset program. Pump P1 in combination with control valve V2 can be used to provide the required pressure in the fluid processing portion of the apparatus. Pressure sensor PS1 is positioned in conduit 11. If desired, an additional pressure sensor (not shown) together with appropriate signal lines can be placed between fluid-processing section 24 and valve V2. Alternatively, PS1 could be placed in this latter position. For manual control of the pressure, the signal from PS1 is transmitted through line 26 to the MC for processing as previously described. For automatic control, the signal from PS1 is transmitted through line 27 to controller C2 which retransmits the signal through line 28 to the MC for the usual processing. Controller C2 is shown controlling pump P1 in order to establish the pressure in processing section 24. It may be preferable to control the pressure, in processing section 24, by means of valve V2 rather than pump P1 in order to avoid disturbing the upstream pressure in conduit 11. Line 29 connects controller C2 with valve V2 for this purpose.

For certain purposes, such as the withdrawal of a specific quantity of blood for the analysis thereof, it may be desired to keep track of the exact quantity of fluid which has been transferred. For this purpose, an integrator I1 can be combined with flow meter FM1 as indicated by line 31. If desired, integrator I1 may be contructed and arranged to transmit a signal to the MC so that control valve V1 will be closed when a sample of the desired size has been transferred into the analytical section 22.

A most important feature of the invention which is indicated only symbolically is that S1, as aforenoted, actually may comprise several sensors which monitor the physiological status of the patient. Where hemodialysis is the procedure to which the patient is to be subjected, it is essential that the blood pressure at the fistula be carefully monitored because an excessive rate of withdrawal can result in collapse of the patient's blood vessels. Depending on the condition of the patient, it may also be essential to monitor his pulse rate, breathing rate, concentration of specific chemicals in the blood, and inherent electrical activity such as by electrocardiograph, etc. The MC must be so constructed that excessive deviation from a corresponding set point for longer than a preset period will result in the taking of protective steps, such protective steps being taken immediately on detection of a dangerous deviation in a crucial variable. The steps may include isolation of the patient, call for an attendant or addition of normal saline or other appropriate medication to the blood stream from a vessel 32 (FIG. 3) through a valve V3.

As aforenoted, isolation of the patient generally involves the termination or interruption of the flow of fluid to or from the patient. This can be effected by the closing of valves or interruption of power to pumps or interruption of gravity flow. As is evident from FIG. 1, closing of valve V1 or cutting power to P1 terminates the taking of blood or other fluid from the patient, and closing a valve V4 (FIG. 3) terminates the flow of blood to the patient. In the device of FIG. 2, closing valve V4 interrupts the flow of fluid from tank 33, thus isolating the patient from the device so far as fluid transfer is concerned.

The emphasis in the above description has been on the taking of blood or other fluid from the patient. It should be noted that a number of procedures involve these steps and the apparatus shown schematically in FIGS. 1-3 is suitable for carrying out such procedures.

It should be emphasized, that the taking of fluid from a patient may also be a part of procedures which involve infusion of fluids to the patient as well. The point is brought out here because embodiments of the invention may be designed only for the taking of fluids whereas other embodiments may be designed for infusion only and still other embodiments may be designed for both taking and infusion of fluids and, optionally, for treatment of said fluids.

Apparatus for introducing fluids of various types, including blood, into a patient is shown in FIG. 2. A fluid, which may be an IV solution, containing medication or nourishment or dialyzed or oxygenated blood or blood components may be introduced into vessel 33 from which it can flow through flow meter FM2 and valve V4 into the patient. In the arrangement shown in FIG. 2 flow takes place by gravity. However, where the fluid to be introduced into the patient is dialyzed or oxygenated blood the flow of the fluid is induced by a pump as will be described in connection with FIG. 3. Preferably, flow meter FM2 which may be a drop-counter has associated therewith an integrator I2 so that the volume of fluid transferred to the patient during the time of treatment will be known. The physiological status of the patient as sensed by sensor S1 can be transmitted directly to the MC or by way of controller C3. Controller C3 controls the rate of flow of fluid into the patient by adjustment of valve V4. It may also schedule a variety of treatments in programmed sequence. As with the system for taking fluid from a patient as shown in FIG. 1, deviation of the rate of administration of fluid to the patient beyond present limits despite the control efforts of controller C3 where the deviation persists for longer than a preset period of time activates the MC to isolate the patient protectively and optionally generate an alarm signal. In the absence of controller C3 a display means 12 indicates the adjustment of V4 (FIG. 2) which should be made by an attendant. The alarm means is indicated by the reference number 34. The signals from S1 which goes directly to the MC passes along line 36 (FIG. 2) while the signal which goes to controller C3 passes along line 37 and thence along line 38 to the MC. Similarly, the signal from flow meter FM2 directly to MC passes over line 39 whereas the signal for automatic control passes over line 41 to controller C3 and thence along line 38 to the MC. Similarly, the signal from flow meter FM2 directly to MC passes over line 39 whereas the signal for automatic control passes over line 41 to the controller C3 and thence over line 38 to the MC. As before, the signal from S1 can be transmitted directly to the MC while the signal from flow meter FM2 can be passed through controller C3 and thence to the MC for automatic control of the valve V4.

Where infusion is sufficiently routine and S1 senses pressure, then S1 may be placed in line 45 as indicated in phantom in FIG. 2. Alternatively, an additional pressure sensor may be placed in line 45, the purpose being to detect pressure changes due to accidental displacement of the needle, for instance.

Conventionally, provision is made for avoiding introduction of particulate material such as clots or of gas bubbles into the patient. Such devices are well known and, where necessary, may be introduced into line 45 for protection of the patient.

The control system, arranged for use in connection with hemodialysis equipment, is shown in FIG. 3. Since hemodialysis involves taking body fluid, namely blood, from a patient, processing the blood and then returning the blood to the patient, many of the components in the hemodialysis system are similar to those already shown in FIGS. 1 and 2. Consequently, certain details, already explained in connection with FIGS. 1 and 2 are not shown in FIG. 3. For instance, the control system based on controller C1, used in connection with flow meter FM1, valve V1 and pump P1 is not shown. As before, blood is taken from the patient through line 11 by pump P1 which transfers the blood to dialysis canister 42, the canister being divided into blood compartment 43 and dialysate compartment 44 by semi-permeable membrane 46. Where the pump is of the known displacement type, the pump itself, in combination with a counting device, may serve as the flow meter. A crucial variable in the ultra-filtration process is the pressure difference across the membrane 46. Pressure is built up by pump P1 and the necessary resistance of flow is provided by valve V2. Control of V2 is effected by controller C2 as shown in FIG. 1. Desirably, flow meter FM2 is disposed in line 47 for return of blood to the patient and flow meter FM2 is joined with integrator I2. The rate of ultra-filtration can be determined by taking the difference between the readings of FM1 and FM2 in order to obtain an instantaneous value for said rate. As for the total quantity of fluid removed from the blood as a function of time this can be determined by subtracting the reading of I2 from that of I1, as a function of time.

Such an integrator, in effect, plots flow rate against time, the area under the resultant curve, as is well known, being the measure of the total flow in the period of time under study. Actually, the integration may be carried out in a separate device as indicated by the reference characters I1 and I2 using appropriate logic or in the MC as part of an overall program. While automatic plotting and integrating devices are, of course, widely available, it is simpler to convert analogue signals from the flow-meter to digital signals and treat these by programmed logic to yield integrated values of blood volume transferred or ultrafiltrate volume as a function of time. An example of logic means suitable for flow integration is that manufactured by Signet Scientific Company of California.

As aforenoted, saline can be added from vessel 32 in the event that sensor S1 indicates the need for increasing the volume of fluid being introduced into the patient. Dialysate may be introduced into the system from an exterior source, using vessel 48 (FIG. 3) as a storage tank. From vessel 48 dialysate is pumped by pump P2 through control valve V2a along line 49. The dialysate then passes through flow meter FM3 connected to integrator I3, thence through pressure sensor PS2 and into the dialysate side 44 of the dialysis containers. The dialysate flow rate is maintained by controller C4 which signals MC along line 50 for control of valve V2a and thus for control of the dialysate flow rate through line 50a. Alternatively, controller C4 can be connected directly to valve V2a for control thereof. Valve V6 provides the necessary resistance to the flow generated by pump P2 in order to establish a desired pressure in dialysate compartment 44 and thereby a desired pressure difference across membrane 46. The pressure in dialysate compartment 44 is read by means of pressure sensor PS2 which transmits the value to controller C5 along line 51 and thence along line 52 to the MC.

As is the case with the other controllers, the MC can vary the set point of C5 in accordance with a preset program. The line connecting the MC to controller C5 for control thereof is not shown. The MC takes note of the readings from both pressure sensors PS1 and PS2 in order to maintain the desired rate of ultrafiltration or to change it as is necessary in accordance with the stage of the treatment and the physiological status of the patient. Controller C5 signals from pressure sensor PS2 along line 51 and transmits to MC along line 52 for control of valve V6 by sending an appropriate signal along line 53. Where automatic controllers are not used, the MC can activate the display means 12 to indicate the adjustment that should be made manually to valve V6. The dialysate, now containing ultrafiltrate and solutes removed from the blood stream passes along line 54 through flow meter FM4 to pump P3. Integrator I4, in combination with integrator I3 makes it possible to determine the quantity of ultrafiltrate which has passed into the dialysate line. It thus can serve as a check on the quantity removed from the blood as indicated by integrators I2 and I1. As is evident, it is not completely necessary to have both pairs of integrators, but it is convenient do to so both as a check, and because individual sections of the system may be used for purposes other than hemodialysis.

Pump P3 serves a double purpose. This pump makes it possible to drop the pressure in compartment 44 below atmospheric, should this be necessary in order to maintain the desired pressure difference across membrane 46. Of course, in such a situation, valve V6 would be wide open. The second function of pump P3 is to establish a desired super-atmospheric pressure in regeneration unit 56. This unit is an optional piece of equipment used in the event that it is desired to recover ultrafiltered solution from the dialysate line. This feature is advantageous where the apparatus is to be portable. In order for a high pressure to be maintained in canister 56, a resistance in the form of a valve V5 is placed in line 57. Valve V5 may either be set manually or by means of a controller and pressure sensor system such as is shown in line 11 of FIG. 1. The water recovered in this way may not be completely pure since some mass transfer may take place simultaneously with transfer of water through the perm-selective membrane (not shown) in regeneration unit 56. However, the quantity of dissolved solids can be kept to a sufficiently low level so that the water recovered in this way can be transmitted through line 57 back to dialysate source 48 where it is mixed with a dialysate concentrate introduced through line 58, the composition of the concentrate introduced through line 58 being adjusted to compensate for the solids in the recovered water. The concentrated dialysate from dialysate canister 56 passes to waste through line 59.

A variety of features, as disclosed in my previous applications, can also be advantageously employed in connection with the apparatus disclosed herein. For example, provision can be made for detecting change in color in the dialysate passing through the dialysis canister 42, such change or development in color indicating leakage of blood through the membrane. As another example, the fluid introduced into the patient through line 47 can be brought to body temperature and provision made for removal of any solids such as clots and of gas bubbles. Saline from vessel 32 in FIG. 3 can be introduced to increase the blood volume or fluid volume where necessary, and introduction of saline can also be used to compensate for variations in the rate of blood flow or other fluid flow caused by accidental influences.

A large number of sensors suitable for use in connection with the present apparatus are available commercially and those skilled in the art are familiar with most, if not virtually all, of such devices. For instance, ion-specific electrodes for identifying various ions such as hydrogen, sodium and potassium in the blood are manufactured by Beckman Instrument Company, by Orion and by Corning Glass Company. Pressure transducers which can be used to determine the pressure in the compartments on either side of a membrane through which ultrafiltration is taking place or in chambers in a modular vessel structure to be described below are manufactured by Statham, by Honeywell and by Bell and Howell. Such a transducer may be in the form of a manometer which can be coupled by means of a stopcock to a line in which arterial pressure or venous pressure is to be measured, or it may be in the form of a strain gauge, especially useful with a disposable dome and diaphragm isolating the electronics from fluid contamination.

The measurement of fluid flow can be carried out by electromagnetic means such as manufactured by Carolina Medical or by Disa. Honeywell also manufactures a device for measuring blood flow rate using thermodilution. A preferred means of measuring flow rate is by means of a pump which pumps liquids at controlled rates with great precision. Such a pump is manufactured by Fluid Metering Incorporated. Another type of flowmeter is that which operates on the variable orifice principle. The position of the indicator in the variable orifice meter may be measured or determined by means of a light beam. This measurement can be recorded and then integrated as a function of time in order to yield the volume flow over a given period. Alternatively, rotating paddles or impellers of various types can be used, such as provided by Signet Scientific Company of California, including logic means for integration.

It should be noted that the manufacture and use of microcomputers has now proliferated enormously due to the fact that the price of the necessary microprocessors or central processing units has been reduced so greatly, thereby making it possible to construct microcomputers for specific purposes such as dedicated process control, where, for some reason, it is not considered desirable to construct or use the microcomputer from available, off-the-shelf components.

Figure 4:
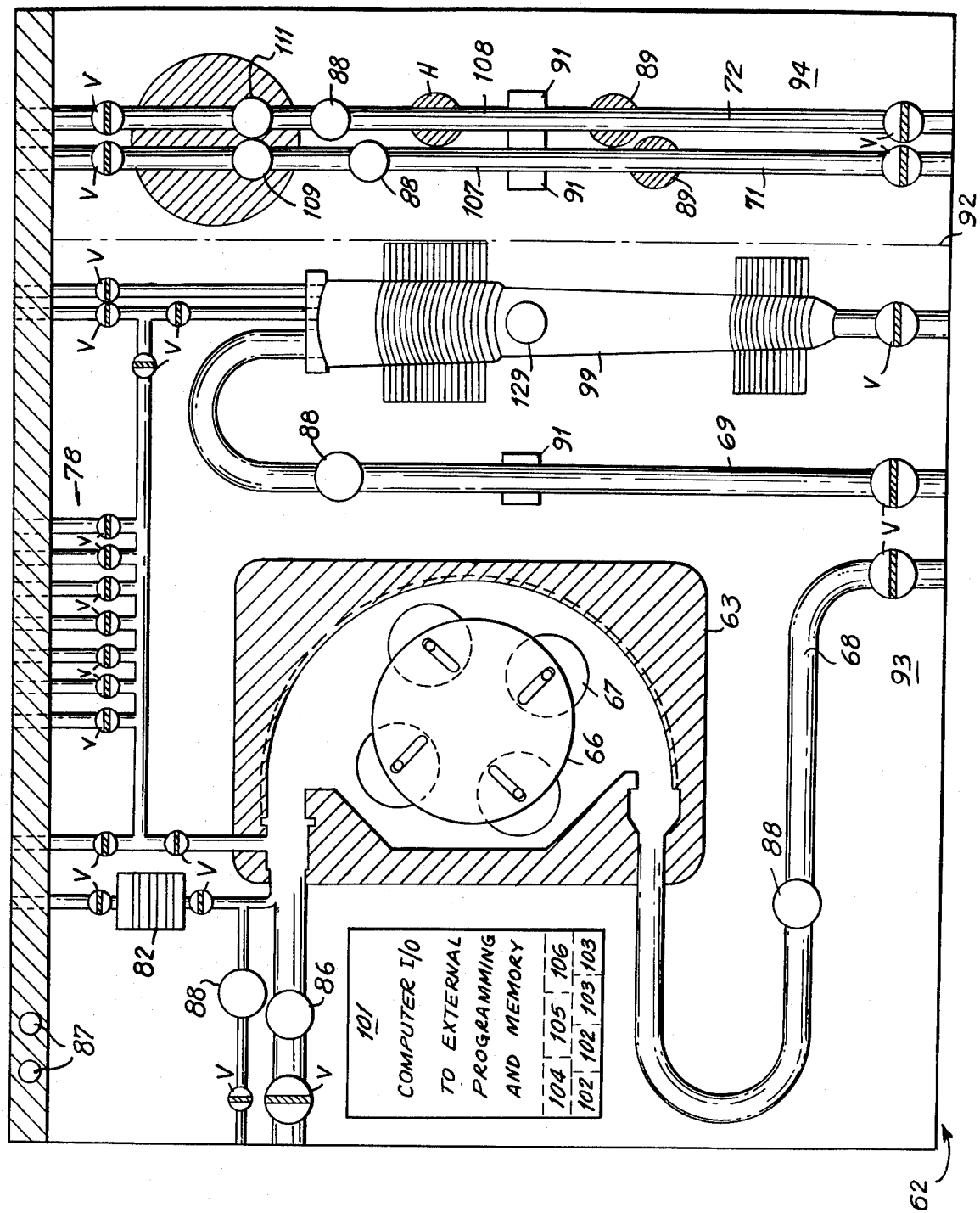
FIG. 4 is a support for holding and operating a modular vessel structure, the support also including sensors for monitoring fluid within the module and for monitoring the patient served by the system, the interface of the support being designed for holding simultaneously two vessels for carrying out two different procedures, it being noted that the two vessels may be combined into one with separate channels and chambers for carrying out the separate procedures.

The apparatus of the present invention is intended for use, generally, in combination with a variety of modular vessel structures, as aforenoted. The portion of the apparatus shown in FIG. 4 is termed the interface and is arranged and constructed for supporting the module and controlling the flow of fluid therethrough. In addition, it holds the sensors for detecting the values of variables relevant to the fluid within the module and for signalling the values of said variables to the microcomputer. Examples of modules are shown in FIGS. 5 and 6, these modules being designed to mate with the interface shown on FIG. 4 and to be supported thereby.

Figure 5:
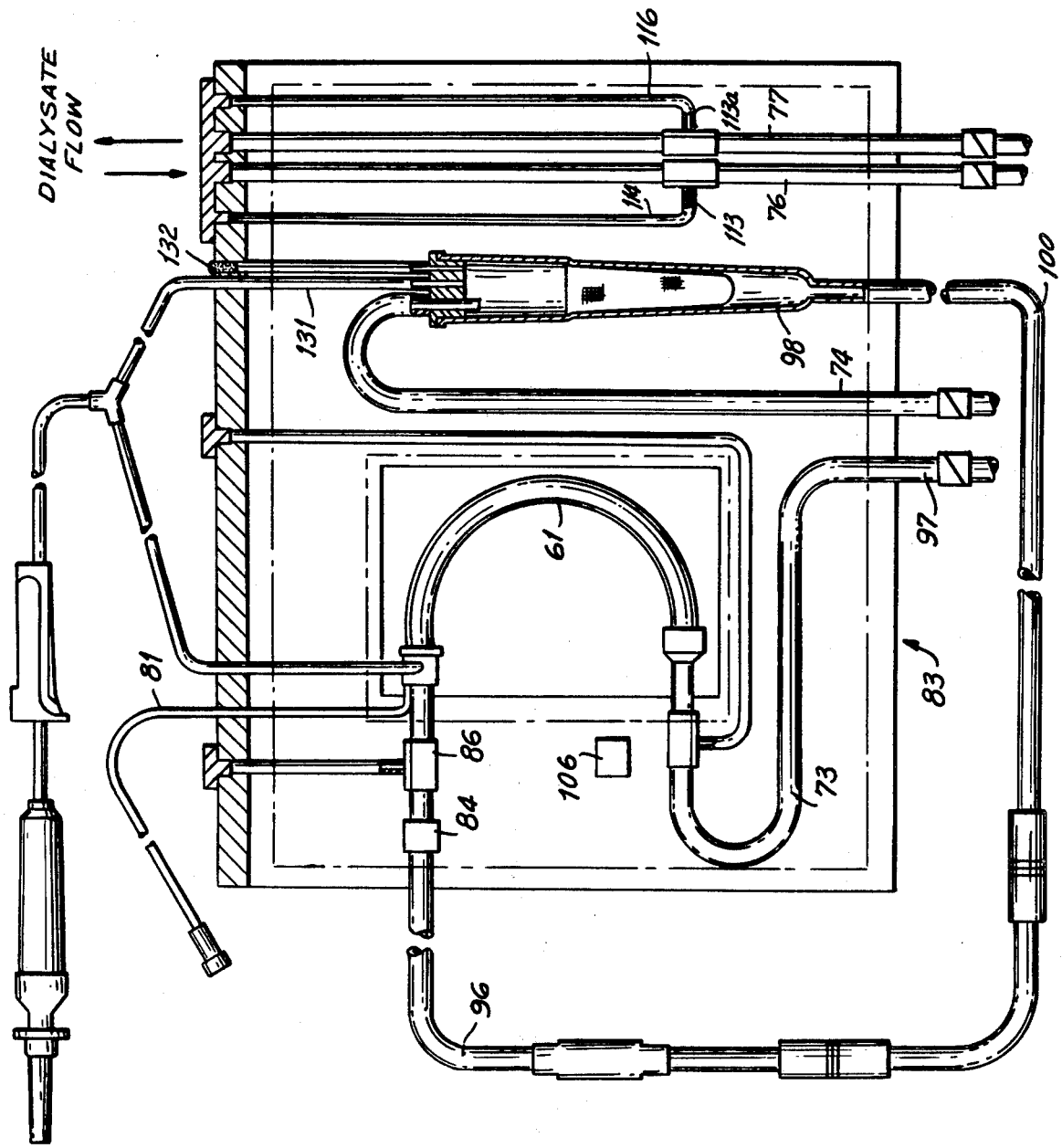
FIG. 5 is a modular vessel structure for carrying out hemodialysis in cooperation with the support of FIG. 4.

In a preferred form, the flow of fluids through the modules takes place through flexible tubing such as the semicircular length of tubing indicated by reference numeral 61 in FIG. 5.

The support portion of the apparatus of the present invention is indicated generally by the reference numeral 62 and, as aforenoted, it is hereinafter termed the "interface". Interface 62 includes a block 63 having a semi-circular depression or groove 64 for receiving a flexible tube 61. Disposed within semi-circular depression 64 is infusion pump 66 which is driven by a motor (not shown) and has rollers 67 for compressing tubing 61 to drive fluid therethrough. In the event of power failure, infusion pump 66 is such that it can be rotated manually.

Figure 6:
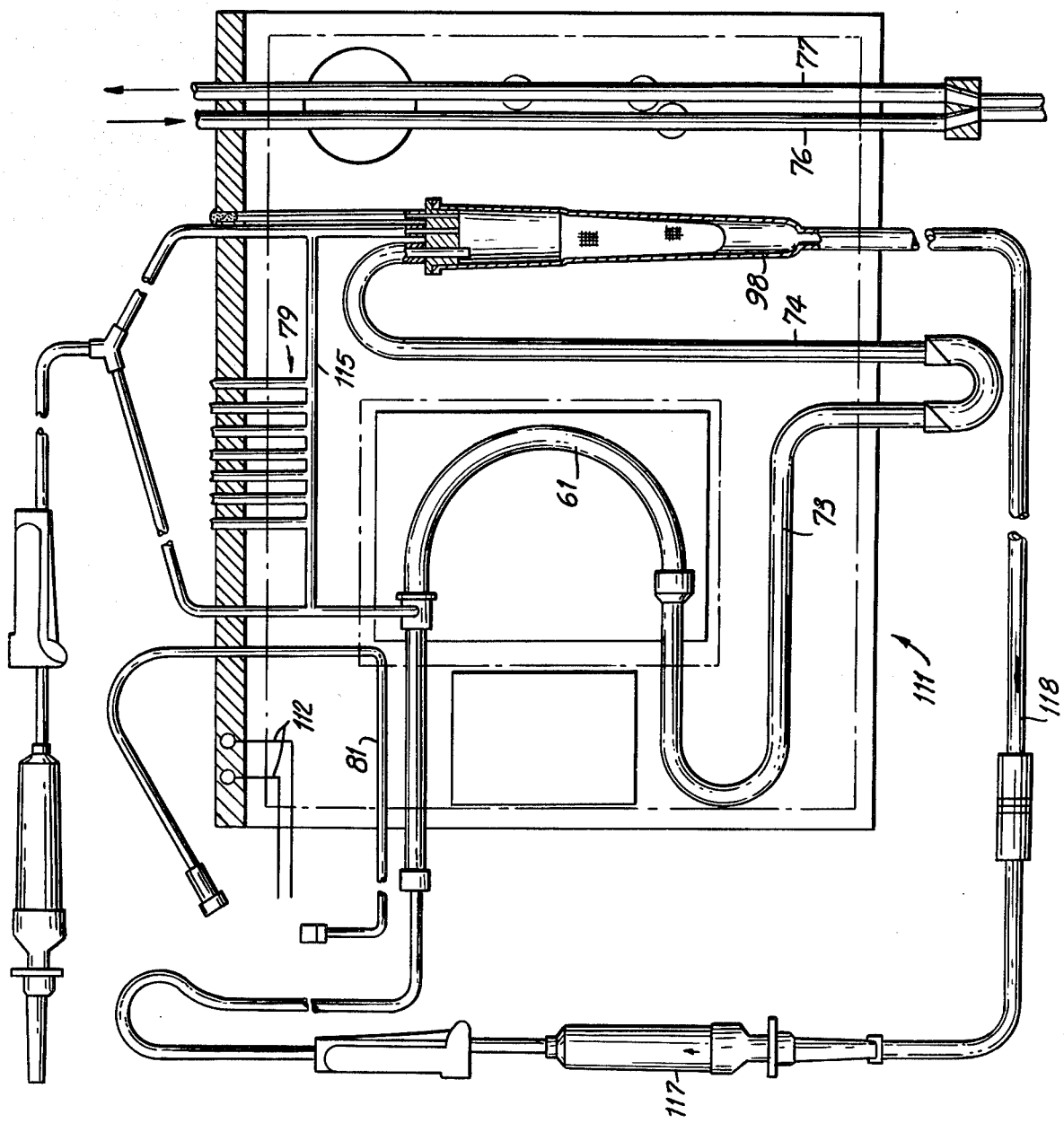
FIG. 6 is yet another embodiment of a module for mating with the interface of FIG. 4.

As will be evident from FIG. 4, interface 62 has grooves 68, 69, 71 and 72 for receiving tubing portions 73, 74, 76 and 77 of FIGS. 5 and 6.

Interface 62 also has a number of grooves indicated generally by the reference numeral 78 for receiving a matching group of tubing sections indicated generally by the reference numeral 79 (FIG. 6) through which different physiologic fluids, such as medications, can be selectively added under the control of the MC.

The module of FIG. 5 includes a length of small-diameter tubing 81 into which an intra-vascular needle connector can be inserted for continuous micro-infusion of medication by infusion pump 82. Alternatively, tubing 81 in combination with a needle connector (not shown) can be used for determining blood pressure in a blood vessel of the patient.

Control of flow of fluid through the module is achieved by means of valves indicated schematically as circles positioned over the grooves and given the reference character V. The module in the various embodiments has flexible portions, whether of tubing or in other forms which seat in the grooves. The valve may then consist of a plunger activated from the rear of interface 62 which compresses the tubing to control the rate of flow of fluid therethrough or to shut it off completely.

For monitoring the flow of fluid through the module and the condition of the patient, both interface 62 and the module, indicated generally by the reference numeral 83, are constructed for cooperation with sensors. Thus, the rate of flow of fluid through tubing sections 61 can be determined from the rate of rotation of infusion pump 66 or by insertion of a calibrated diaphragm pump 84 in an extended portion of tubing 61. The pressure in tubing 61 can be determined by means of a pressure sensor 86 mounted on interface 62. The pressure sensor may be in the form of an ultrasonic generator and detector.

Interface 62 may also carry electrode contacts 87 for monitoring electrical characteristics in the patient where such activity may be due to inherent electrical activity such as electrocardiograph signals, or physiologically induced alteration in the electrical characteristics of a circuit including a portion of the patient, such as the impedance change, or the signals from complex sensors such as ion-specific electrodes. Such functions may be included in the design of a procedure or in the module itself.

The measurement of pressure in the various ducts and channels and reservoirs in different type of modules has an additional significance because pressure differences can be translated into flow rate (by combination with a flow resistance, not shown) as well as into intravascular pressure. Additionally, pressure sensors are shown in FIG. 4 as circles superimposed upon grooves and given the reference numeral 88. Flow rate sensors, indicated by the reference numeral 89, may consist of pressure sensors in combination with appropriate flow resistance such as an orifice, as aforenoted, or electromagnetic devices, paddle-wheels or calibrated pumps. In many operations it is also important to determine the temperature of a fluid being circulated especially where such a fluid is infused into a patient; such temperature sensors are indicated by the reference numeral 91 and are to be taken as including, where desirable, heaters and cooling devices for raising or lowering the temperature of the blood (according to programmed settings).

Interface 62 is shown schematically as divided into two portions by dashed line 92, the portion of interface 62 to the left of line 92 having the reference numeral 93 and the portion to the right having the reference numeral 94. Left portion 92 can accept a module suitable for hemoperfusion. Blood is taken from the patient through tube 96 which is connected to the patient through a needle (not shown) into an artery, or preferably, an A-V fistula. After circulating through tube 61 under the urging of infusion pump 66, the blood is passed through tube 97 to a column containing a suitable adsorbent. The blood is then returned through tube 74 to debubbler 98 which is held in recess 99 of the interface and finally returns to the patient through tube 100. Left portion 93 of the interface is also shown as holding microcomputer 101 which generally includes analogue-to-digital and digital-to-analogue converters (102), controllers 103 and display device 104, it being recognized that controllers 103 may also serve as display devices. Interface 62 may also have mounted thereon, code-detector 105 which is sensitive to code 106 on module 83, code 106 indicating the nature of the procedure for which module 83 is constructed. Code-detector 105 is shown as part of microcomputer 101 to indicate that the computer is constructed for comparing the code of the module with a program entered into the computer for carrying out a specific procedure and thereby insuring that the program and the module correspond. Needless to say, the computer (and its program) contains the necessary elements for operating the interface and controlling the flow of fluid through module 83 and insuring that the procedure is carried out as programmed.

Right side 94 of interface 62 (FIG. 4) can accept a module (not shown) designed either for taking a fluid from a patient say through a tube in groove 107 or infusing a fluid into a patient, say through a tube in groove 108, the fluids being driven by pumps 109 and 110, respectively, through openings in the interface. Alternatively, where the fluid is to be infused, said fluid may be gravity-fed. This portion of the interface is particularly suitable for irrigation, where it is desired to monitor production of fluids within the patient as is the case in irrigation of the bladder. In such case, flow-rate sensors 89 can determine differences in flow-rate and are to be considered as including the integrators so that the total quantity of fluid passed through tubes in grooves 107 and 108 as a function of time may be made continuously available. In this way, production of urine by a patient can be determined even though the bladder is being irrigated by a substantially larger quantity of fluid.

Infusion of IV fluid is a particularly important medical procedure which is called for in the treatment of a wide variety of pathological and traumatic conditions. Infusion may be used for alimentation, for increasing blood volume as in transfusion, and for scheduled, intermittent introduction of specific medications. Module 111 (FIG. 6) includes a manifold header 115 and branch tubes 79 through which a variety of medications in solution, of course, can be introduced into header 115 and thence into the fluid being pumped through tube 61. Flow through branch tubes 79 is controlled by the valves V located in grooves 78. Module 111 is also shown as containing electrodes 112 for connecting with electrode contacts 87 in the interface. Pressure sensors may also be used in connection with module 111 in the same way as shown in FIG. 5 at 113 and 113a. Pressure values may be transmitted through auxiliary tubes 114 and 116, through a connection (not shown) to the microcomputer.

Blood-taking tube 96 and blood-returning tube 100 in FIG. 5 are shown as being connected. Similarly, blood transfusion inlet 117 and infusion line 118 (in FIG. 6) are shown as being connected, such connections being useful for priming prior to the start of a procedure. The module of FIG. 5 is particularly advantageous for hemodialysis, the portion of the module lying over the left portion 93 of the interface serving for flow of blood and the portion lying over the right portion 94 of the interface serving for flow of dialysate, it being noted however, that the dialysate circuit can be part of the interface. Module 111, on the other hand, is advantageous for blood transfusion, infusion of fluid and, simultaneously, for irrigation or lavage. Needless to say, the two portions of module 111 could be completely separate, each carrying its own code for comparison with the program inserted into the computer.

Preferably, the microcomputer is constructed for receiving a program in a standardized format, as in PROM memory or on various types of media, such as magnetic disc or cards, or a combination of these or other standard media such as paper tape, optical scanning codes. Moreover, the module may contain the program as on such media either separately, or as part of code 106.

The medical care system of the present invention can be designed for treatment of patients with profound physiologic disturbances, such as cardiovascular shock syndromes, as well as the treatment of patients with minor disturbances. Shock conditions can be associated with a variety of etiologies due to loss of blood or physiologic fluids, as for example, in surgery, postsurgical recovery, trauma, hemorrhage, gastrointestinal obstruction, diabetes mellitus, diabetes insipidus, adrenal insufficiency and burns. Shock may also result from disturbance of vasomotor activity and cardiac output either iatrogenic or from myocardial infarction, valvular diseases, cardiac arrhythmia or fluid distribution imbalance as in endotoxin shock. Renal, hepatic and pulmonary insufficiency and auto-immune diseases are other examples of conditions requiring intensive monitoring and precise control of therapy including extra corporeal circulation and treatment of body fluid that are amenable to treatment with the system of the present invention.

The system has already been described in connection with hemodialysis, infusion and irrigation. The dialysate/ultrafiltration monitoring and control system is also adapted to monitoring fluid drainage, gastrointestinal tube suction, biliary or wound drainage by way of catheter, either with or without continuous irrigation. The use of irrigation for continuous urinary bladder drainage by catheter to reduce the incidences of infection is a standard procedure, but precludes accurate assessment of urine output. It has not, therefore, been used in shock patients despite the fact that the output of urine provides a good indication of the adequacy of tissue perfusion with blood. Monitoring the difference between the inflow of irrigation fluid and the outflow, as with the control and monitoring of dialysate to measure ultrafiltration as shown in my previous patents, will allow either irrigation or urine measurement or simply, urine output monitoring by the system, with inflow set at zero and output pumping controlled by pressure.

The system can, of course, be adapted by inclusion of an appropriate catheter such as the standard "Swan-Ganz" to monitoring the pulmonary capillary wedge pressure, in this unit using the arterial blood pressure line and pressure transducer, or with modifications of the system, including programming one of the other infusion system lines and pressure transducers. Furthermore, provision may be made in the hardware to connect two or more parts of the apparatus electronically under a single microcomputer to provide additional functions as required, such as use of two pressure-monitoring systems for simultaneous measurements. This will be discussed below in the description of the electronic system architecture utilizing the "data bus".

For a shock patient in addition to monitoring blood pressure and urine output, pulse rate and the cardiac electrical pattern are useful parameters of physiologic function that are easily integrated into the programmed therapeutic algorithm. Techniques of calculating heart rate from the peaks of electrical activity are standard monitoring unit functions and rate calculations are part of the various available computer ECG interpretations. With the use of ECG interpretation programs to indicate the types of arrhythmia, the system can be designed and programmed to treat automatically such life-threatening conditions, as well as to generate an alarm.

The system may be arranged to monitor a variety of procedures, this capability being enhanced by the fact that the interface can be constructed so that the various sensors can be "plugged-in" at different points depending upon the requirements of the specific procedure and the specific module design. Thus, the pressure sensor 88 shown as being in groove 68 can be moved for reading the pressure in a tube lying in groove 108, if desired. Alternatively, the opening for a pressure sensor in groove 108 can be used for a temperature sensor, if desired. Thus, interface 62 can provide substantially more functional points than may be necessary for a specific procedure. Through the use of these multitudinous points and removable sensors, the number of procedures which can be administered by the system is greatly increased. For instance, the system can be adapted to monitoring simultaneously, arterial and pulmonary capillary wedge pressures. Such measurements can be used to optimize the treatment of cardiogenic shock by precise computer control of vasodilator and cardiotonic drugs to reduce myocardial work without sacrificing tissue perfusion. This form of therapy is currently available, but the cost thereof is essentially prohibitive. The apparatus disclosed herein can make such complex care readily available and at relatively low costs.

Further applications of the design principle of the present invention, utilizing appropriately constructed disposable modules, and additional sensors, if necessary, can provide for withdrawal of blood samples for analysis, such analysis being carried out by chemical or by substance-specific electrodes, and the results of the analysis being used to guide computer-controlled drug infusions. Assay of blood characteristics and chemistry including urea, glucose, electrolyte, blood clotting, osmolality or arterial blood gases, can, for example, be used to monitor and control treatment, including as discussed below, multiple hormone and drug administration in complex patterns, as well as extracorporeal circulation and treatment of blood.

Figure 7A:
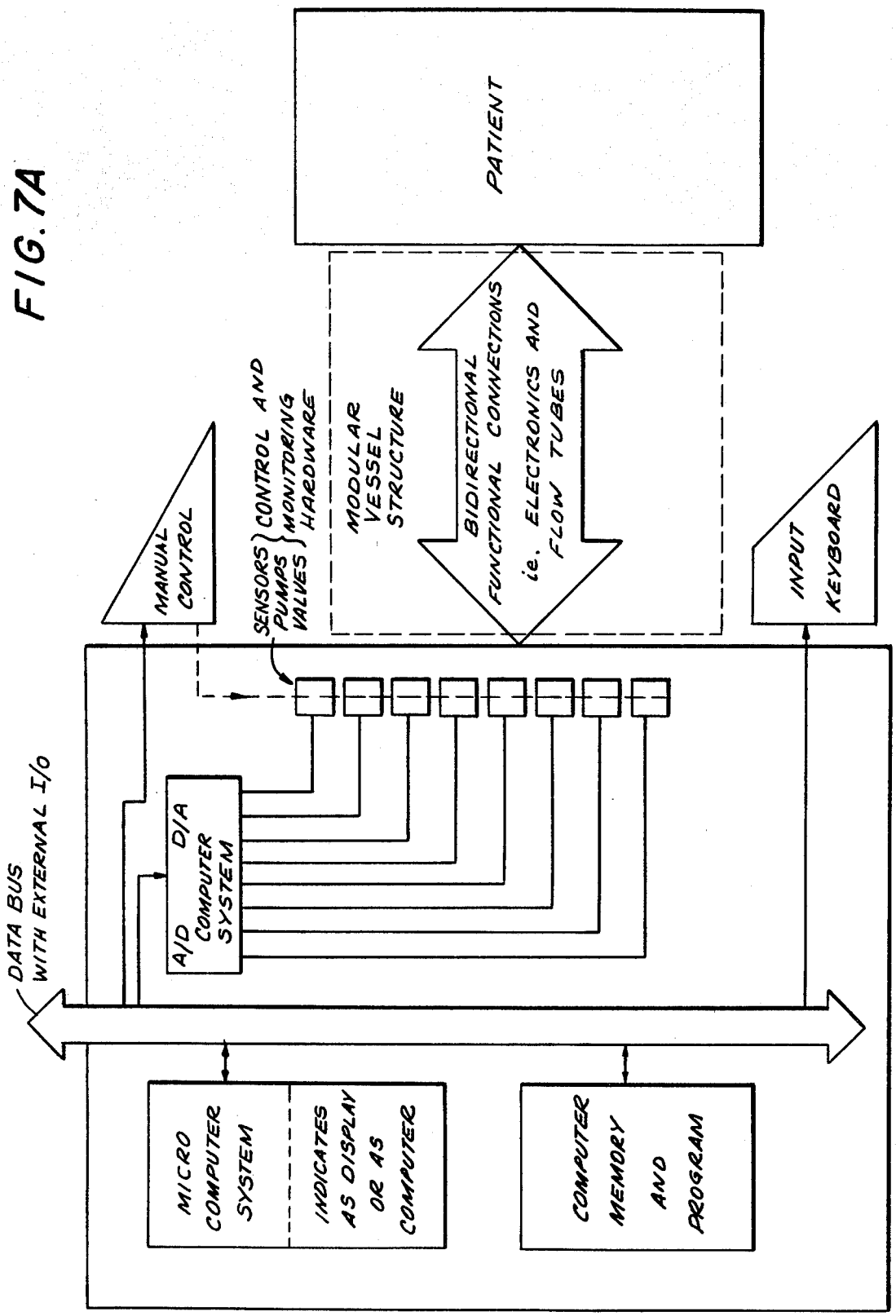
FIG. 7A is a schematic diagram of the intensive care system of the present invention.

FIG. 7A is a schematic representation of the apparatus, using rather standard notation for the electronic information processing components. The structure of this portion of the apparatus is based upon the "data bus" concept common to most modern computer designs. The various computer manufacturers use individualized structures, but in principle their operations are similar. Bi-directional information transmission is controlled by the central processing unit of the computer system, by either time or programmatic priorities given to the data of specific input or output devices. Computer systems such as the Digital Equipment Corporation (DEC), LSI 11 Microcomputer System, based upon the "Q-bus", or the Intel "Multibus" for its SBC 80 Microcomputer System, can be purchased as assembled units to provide the microcomputer functions, when appropriately programmed. This programming is facilitated by the "Bus" architecture because these components, as well as others, provide the "bus" compatible digital-to-analogue, and analogue-to-digital converters necessary for functional integration of the various analogue sensor and controller systems. This facilitates the programming of microcomputer functions because the analogue output of a sensor, for example the blood inlet line pressure sensor, is periodically converted to a digital value and stored at a prespecified address in the converter or computer memory. When a parameter of control, such as the blood pump rate, must be adjusted according to this sensor variable, the data are queried from memory by the central processing unit (CPU) of the computer as an input variable for the controller program that, in turn, calculates a digital output variable. This controller output is similarly stored in memory, at a prespecified address, until the CPU queries the address for the digital variable and sends the information to the appropriate digital-to-analogue converter, where it is translated into the control voltage necessary to operate the system. In the example of the blood pump given, this would be the control voltage for a stepping motor subordinate control system governing the speed of the blood pump to be proportional to the blood inlet pressure.

The A/D and D/A components are standard manufactured devices specifically designed to function with a given computer manufacturer's "bus" architecture, such as the Intel SBC 711 Analog Input Board, SBC 724 Analogue Output Board, and the SBC 732 Combination Analogue I/O Board, of the DEC ADV11-A, KWVII-A, AAVII-A, DRIVII devices. In order for the computer system to function, there must be a pre-established system for specification of the necessary input and output devices, and bidirectional interface functions between the patient and the analogue-digital sensor-controlled systems.

In this patient Interface portion of the apparatus, constructed with all usual and suitable patient protection features such as electrical isolation circuitry, the bidirectional monitoring functions may be of three types:

1. Electronic sensing via placement of electrodes on the patient to transmit signals of physiological electrical activity, such as ECG, EEG, EMG, for amplification and display or as input to interpretative computer programming.
2. The application of voltages or current via bidirectional patient electrode systems will allow measurement of variations in impedance, resistance, capacitance or voltage created by physiological functions, such as thermocouple temperature sensing, or volumetric and plethysmographic sensing, of tissue or body volume changes, as with pulsatile blood flow or respiration, or variation in skin conductance, due to variation in surface electrolyte concentrations as a measure of sympathetic nervous system activity.

3. Interactive electrodes, such as the standard ion-specific or substance-specific electrodes, with or without coupled chemical reaction systems, which are sensitive to pH, sodium, potassium, chloride, calcium, oxygen, carbon dioxide, glucose and urea, these parameters being useful for monitoring many intensive care procedures.

It will be noted that FIG. 7 shows a bidirectional functional connection between interface 62 and the patient. The term "bidirectional" is used to indicate that the interface controls flow of fluid to and from the patient and provides for signals from the patient to the microcomputer which influence the course of a procedure under way. Further, the diagram of FIG. 7A shows an arrangement which includes manual control of the various pumps and valves should it be desired to control these functional points non-automatically. Where manual control of the valves and pumps is to be used, then an indicator for showing adjustments or changes to be made is needed. The indicator may be in the form of a meter, CRT, LED or liquid crystal display or an alarm signal calling for protection of the patient by shutting valves selectively, etc. The preferred indicator means is an alpha-numeric display which either indicates or specifically states adjustments to be made, the display being operated by the microcomputer. Preferably, control is effected automatically by the microcomputer, the indicator means then being a controller which may be either internal or external to the microcomputer with parallel display as desired.

The use of electronic communication between the microcomputer and the control elements makes it possible to construct the system in a wide variety of embodiments. Thus, two different systems, one being designed for infusion and the other being designed for taking fluid from a patient can be connected as shown schematically in FIG. 7B for carrying out a procedure requiring both the taking of blood and the returning of blood as in hemodialysis. As indicated in FIG. 7B two medical care systems in accordance with the present invention and indicated by the reference numerals 119 and 121 can be connected by a bus 122 for bidirectional communication of signals from sensors and signals to control elements. In a hospital where a plurality of such devices are simultaneously in use, for a single patient or multiple patients, the bus 122 can be used for communication with a central monitoring system 123 by means of which all of the procedures taking place in the institution can be monitored and, if desired, recorded. Although systems 119 and 121 are shown as each having its own microcomputer, the microcomputer 124, in a preferred embodiment, can control the procedures being carried out by systems 119 and 121, thereby reducing the number of microcomputers needed. As is evident, either a central microcomputer or a microcomputer associated with each subordinate system may be preferable depending on the specific situation.

Module 83 of FIG. 5 can contain the structures and reactants necessary for other physical measurement and control systems such as determining physiologic parameters or controlling therapeutic actions by means of the transmission of hydrostatic pressure from a patient's vasculature to a remote sensor using a tube filled with an essentially incompressible liquid. Such a hydraulic system can be operated as shown in connection with the debubbler which fits into recess 99 of the interface. The pressure within the debubbler can be determined by sensor 88 associated with groove 69. Such a debubbler is particularly valuable in connection with extra corporeal circulation utilizing module 111 or module 83. Where hemodialysis is to be carried out, either a flat-plate hemodialyzer or a tubular membrane hemodialyzer may be used, convenient arrangements of the debubbler and the hemodialyzer being shown in FIGS. 8A and 8B. In each case the debubbler may be supported on the hemodialyzer canister 126 or 127. Preferably, the debubbler also includes a filter 128.

In a preferred embodiment, a level sensor 129, which may be optical, ultrasonic or capacitative, is provided for monitoring the level of the liquid in the debubbler. Should the level drop too low, saline can be added quickly through tube 131 (FIG. 5). Should the pressure in the debubbler become excessively high, vent 132 can be opened. Obviously, these adjustments can be made either automatically by means of a controller or manually by an attendant on command from the controller.

The construction of FIG. 8A can be used for oxygenation of blood or transfer of other gases by the use of a membrane which is selectively gas-permeable. Such membranes are now well known and available commercially and transfer of oxygen in one direction and carbon dioxide in the other can be carried out, and direct exchange of other gases such as anesthetic gases can be performed.

The system of the present invention is readily suited to diagnostic testing, especially testing involving analysis of fluid taken from a patient. The module for carrying out such an analysis and the apparatus are shown schematically in FIG. 9 in which 133 is a valve for controlling the taking of a fluid through duct 134 from a patient, the patient's physiological status being monitored by microcomputer 101 through sensor 136 which may be noting any of a number of variables indicative of the condition of the patient. The sample of fluid taken from the patient is transferred by pump 137 in the interface of the apparatus, the sample being directed to assay chamber 138. The assay chamber may have therein a reagent, and one or more reagents may be transferred from an equivalent number of reservoirs indicated by the reference numeral 139. The results of the reaction with the reagent or reagents can be noted in a variety of ways, the combination of light source 141 and photoelectric cell 142 exemplifying a spectrophotometric method which can be controlled by the microcomputer 101. Control of the light source and the photoelectric cell is indicated schematically by lines 143 and 144; similarly, control of pump 137 is indicated as being mediated by controller 146. The results of the test calculated by the microcomputer from a sensed rate of change in transmission of light through the reaction mixture can then be displayed by the microcomputer using alpha-numeric devices such as an LCD, print-out or a CRT.

In the transfer of a body fluid for analysis, in general the method of pumping is relatively unimportant. It is only significant that the quantity of fluid taken and transferred to the reaction chamber be precisely known and that the rate of taking fluid not be so rapid that the patient suffers distress. However, there are a number of procedures in which the method of pumping can be of great importance. Specifically, where blood is to be taken from a patient and then returned, it is essential that the pumping technique be atraumatic, that is harmless so far as blood cells are concerned. The roller pump 66, shown schematically in FIG. 4 is so constructed that the tube is never closed completely by the individual rollers so that the destruction of blood cells is avoided. In addition, the pulsatile flow produced by such pumping or by pumping with so-called "finger pumps" is particularly useful in procedures which benefit from a transition from laminar flow to turbulent flow and back again. For example, pulsatile flow during infusion may be simulating the natural process to improve the patient's physiologic response. Also, where there is instantaneous cessation of flow, it is possible to determine the vascular pressure of the patient without the error caused by pressure drop due to line resistance to flow. A further advantage of pulsatile flow is disclosed in U.S. Pat. No. 3,616,926 at column 3, line 47, which states that "the membrane-clearing capacity of laminar flow skimming can be augmented by providing for either pulsatile flow or alternate synchronized internal pumping". The use of pulsatile flow to initiate mixing in a flowing fluid, through the introduction of turbulence is especially appropriate in flowing blood, as for example in hemodialysis to reequilibrate the plasma concentration gradient of the boundary layers to improve the mass transfer characteristics of the system, while intermittent laminar flow aids in keeping the membrane pores unclogged. Conversely, in applications such as oxygenation, the pulsatile flow-induced turbulence will provide mixing of blood cells into the boundary layers, increasing the rate of gaseous equilibration when blood is flowing in a physiologic gas-exchange device, such as a membrane oxygenator, while similarly allowing the membrane-clearing effect of intermittent laminar flow, the relationship between laminar and turbulent flow being a function of the flow rate and flow path configuration.

The pulsatile flow mode allows the line pressure sensor to have dual functions. As noted previously, at low flow rates, signals to the MC from sensor systems such as pressure sensor 86 in groove 68 of FIG. 4 yield a measured pressure which is representative, for example, of the patient's intravascular pressure at the point of access. In the case of application of the system to hemodialysis, using a "fistula" access, the mean fistula blood pressure will be below, but proportional to the patient's arterial blood pressure, as there is a close direct arteriovenous connection to provide the blood flow necessary for extracorporeal blood circulation. This sensed data can be input to the microcomputer program adjusting the procedure according to the patient's physiologic status. These pressures, and their subsequent changes, in the course of blood pumping and treatment, can be stored for comparison and evaluation, since an original pressure measurement would represent the baseline for a particular procedure, and subsequent measurements would therefore represent deviations from baseline. Secondly, since the fistula blood pressure, in hemodialysis, is a major variable in the potential rate of extracorporeal blood pumping, the line pressure sensor, functioning to control the rate of blood pumping will automatically compensate for changes in the fistula blood pressure; hence the patient's arterial blood pressure and physiologic status, sensed through this basic relationship, may be refined through programmed comparisons to improve its sensitivity by including other sensor data such as the pulse rate, or changes in its rate, which usually increases to indicate decreasing blood pressure via a physiologic compensatory mechanism maintaining tissue perfusion, while the pulse rate decreases with increasing pressure.

Data collected from specific sensors appropriately digitized as previously described can be used as input to the programming algorithms relating parameters such as the pulse rate and its rate of change to the mean fistula blood pressure or the pressure of fluid available for pumping at the point of entry into an extracorporeal diagnostic or treatment system. The microcomputer processes the information received from the various sensors and controllers, for example, calculates, from programmed relationships including those related to patient's physiological functions, the necessary prompting of manual actions and guidance of personnel activities, or calculates the digital representation of analogue output to control the rate of fluid flow by means of the pump rate control system previously described, or to control the course of fluid flow by the actions of the control valves.

Where one or more subordinate controllers are provided, signals from sensors can be transmitted directly to subordinate controllers which may be designed to accept the analogue sensor output directly, or to receive the digitized sensor signal, with dedicated internal signal processing systems and programming to utilize the signal to establish the set point or operating parameters of the controller's function.

It will be noted that in a complex procedure the rate and quantity of data supplied by sensors are sufficiently great so that it would be virtually impossible for one attendant to be able to determine what adjustments of the procedure may be necessary, so that the microcomputer is essential for carrying out this phase of the operation. In addition, it can be extremely difficult for an attendant to carry out the adjustments under the instruction of the microcomputer in certain procedures so that automatic control of the procedure by the microcomputer constitutes a substantial advantage.

The complexity of certain procedures can be great, depending upon the needs of the patient. The number of procedures which can be carried out is similarly great. Consequently, it must be noted that FIGS. 1, 2 and 3 are schematic for purposes of convenience and simplicity. Conduits for directing fluid flow are shown as solid lines, and signaling lines between sensors, controllers and the microcomputer are shown as dashed lines, and control signals from the MC or the subordinate controller are shown as dot-dash lines. As must be evident there is no reason to limit the possible pattern of interconnections to those shown. In fact, in the use of the standardized "bus" architecture to simplify construction of the digital electronic information processing components, there is another significant advantage.

As described previously, using random access computer memory, or other memory devices, accessible to the MC via the "bus" with a specific programming sub-routine for "memory mapping" to receive and provide data for other programming sub-routines, the specific function of an analogue or digital device and its hardware can be specified by computer programming, for example, specifying that in the desired procedure a pressure sensor measures arterial blood pressure, a particular pump provides infusion of saline, thus obviating the necessity for complex wiring, switching and relatively limited function devices to provide the combinations of analogue device functions necessary to perform a large number of different, complex procedures. This is further facilitated by, though not dependent upon, the use of disposable modules designed to match the specific programming functions, such as providing the connecting fluid passage between a pressure sensor specified to signal the pressure of a particular pump and the pump outlet.

For example, with another programmed routine and a disposable component leading from an appropriate source of physiologic fluid to a patient's vasculature, the pump 66 could be reversed for controlled infusion of the fluid with pressure control and measurement of the outlet pressure at the point of vascular access, such as an arterial blood pressure, or with appropriate placement of properly-designed catheters, venous blood pressure at various points in the patient's vasculature or pulmonary capillary wedge pressure reflecting the heart's left atrial pressure. These all can be useful significant parameters in monitoring the physiological status of patients undergoing various diagnostic or therapeutic procedures.

The controlled infusion of drugs, to reduce or increase vascular constriction in control of blood pressure, cardiac work load, and to provide balanced tissue perfusion, can be used to optimize the recovery of cardiac muscle and function after vascular occlusion results in myocardial infarction. Muscle death results from insufficient vascular perfusion with anoxia and metabolic waste product accumulation. The degree of anoxia and waste accumulation, however, is related in part to the work load stress applied to the muscle cells. Since cardiac work is in part related to the pressure that must be generated by muscular contraction to pump blood through various tissues, it appears that reducing the work load of marginally-perfused heart muscle by reduction in the pressure required will maintain cellular viability long enough for compensatory physiologic changes to develop, such as opening collateral blood channels. One therapeutic method by which this can be accomplished is with controlled infusion of vasodilator drugs. This requires constant monitoring of parameters such as those described, especially blood pressure and heart rate, making the procedure complex, labor-intensive and, therefore, expensive. These factors significantly limit its availability to patients. The basic combination of pumps and sensors, controllers and a microcomputer, with an appropriate module and necessary programming, as taught herein, and desirably including patient safety features as previously described in '731 for maintaining the infusion line free of air bubbles, microemboli, temperature, etc., can easily overcome these difficulties to provide this, and other complex forms of treatment and diagnosis. Also, portions of this apparatus, in combination with a microcomputer, may also be of value for a limited range of procedures.

These possibilities are, of course, a major, but not essential, advantage of this improved apparatus for medical diagnostic and therapeutic procedures, significantly reducing the cost of making various sophisticated procedures available using relatively limited hardware designs that can be adapted to multiple procedures by programming specification of apparatus functions and integration with appropriately constructed disposable components. It is, of course, theoretically possible, but undesirable, to reuse a sensor-controller interface, unless economic conditions seriously and significantly outweigh the risks of inter-patient contamination and the inconvenience.

Further examples of more general types of applications envisaged, though by no means exhausting all potential applications, will be described below, as the examples cited are only some of a number of applications that can be developed from a single modular component by programming adjustments. This further enhances the potential economy of the system, limiting the number of different module constructions required for a large number of procedures, with their adaptation for different procedures the result of the interaction of programming and the active agents, such as drugs, contained within the module.

Figure 9:
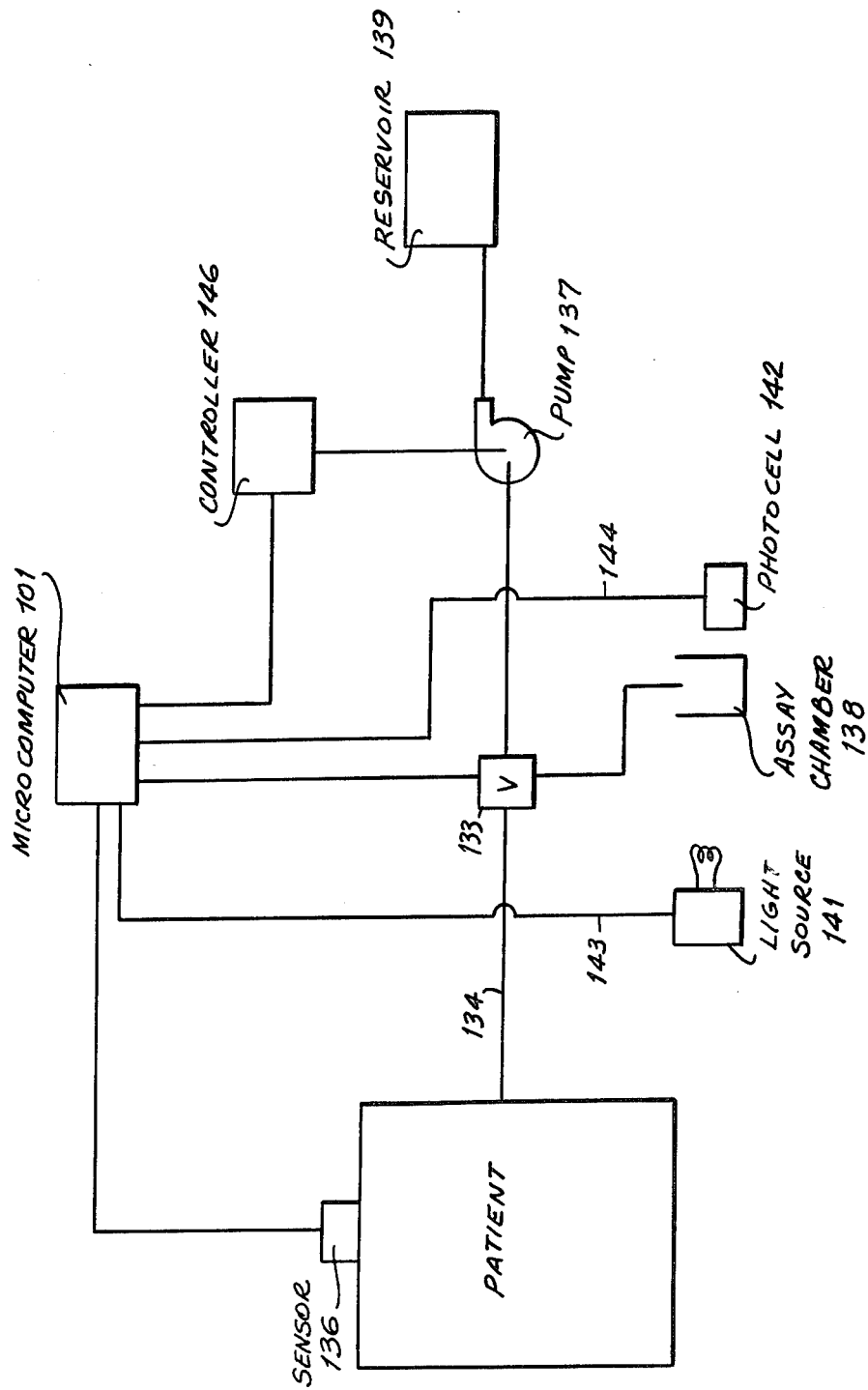
FIG. 9 is another embodiment of a fluid analytic system.

The flexibility of the medical care system is also exemplified in FIG. 9 in which microcomputer 101 first directs pump 139 to withdraw fluid from reservoir 139 to fill the fluid flow path 134. This line is then connected to the source of fluid to be analyzed and the pump is reversed under the direction of the MC to withdraw the fluid to be analyzed into the flow tubing which will have a known structure. The known and programmable pump rate and volume relationships will determine the volume of fluid necessary for the analysis which is then pumped into the portion of line 134 which is downstream from valve 147. Valve 147 is then adjusted by MC to direct the flow of fluid to be analyzed and to direct the flow of reagent fluid to the analytic portion of the module by controlling the direction of flow and rate of flow generated by pump 137. A controlled fluid volume appropriate to the predetermined required reaction mixture, for example the volume of fluid to be analyzed plus water necessary to mix with and dilute the reagent already in the assay chamber, is directed to the chamber, thus activating the reaction at a definite, controlled time. The MC records this time and it can then control the measurement of the reaction rate by timed recording of the output of photomultiplier/spectrophotometer 142, in response to controlled light from source 141. Using the appropriate sensors, built into the interface, analysis of diverse physiologically significant chemicals can be carried out, such chemicals being exemplified by glucose, urea, a variety of enzymes and ions. In addition, analytical data can be obtained to be used in the programming of the MC for control of appropriate sub-routines to cover related functions, such as the infusion of fluids or drugs, insulin, for example, in response to glucose or to govern the termination of a process, such as hemodialysis, when the treatment has sufficiently reduced the assayable concentration of specific compounds such as urea. The analytical portion of the apparatus can, of course, include other standard types of devices, such as analytical electrodes, ion specific electrodes, membrane bound enzyme-coupled electrode systems, or secondary analytic processing systems for addition of reagents and manipulation of the reaction fluids. The electrode systems sense the composition of the diluted fluid samples. The system and the modules can be constructed in accordance with the principles of fluid manipulation outlined above so that the module can be constructed primarily for analysis or for analysis in conjunction with treatment of the patient. For example, periodic blood samples from a patient undergoing dynamic evaluation of the pituitary gland's physiological response to infusion of thyrotropin-releasing hormone (TRH), are drawn into the assay system at programmed intervals after injection of TRH to stimulate release of the thyroid stimulating hormone (TSH) from the patient's pituitary gland. The fluid is then assayed for TSH as by the technique of radioimmunoassay. For example, it should be noted that a module for carrying out the RIA can readily be accommodated by the interface.

A three-way valve 23 is disposed in conduit 11. When appropriately oriented, the valve 23 directs fluid for analysis to analytical section 22. Alternatively, valve 23 can be oriented to direct fluid toward fluid processing section 24. An example of the application of this system would be in the taking and processing of blood for storage and subsequent reinfusion or transfusion to another individual.

Withdrawing blood from a donor requires that a sample be obtained for typing and cross-matching with a potential recipient, via the analytic portion of the system. The volume of blood to be processed for storage can be directed via MC programming to the fluid-processing portion 24, FIG. 1. This processing may take the form of addition of blood to a reservoir 24 containing an anticoagulant-preservative such as citrate, for routine storage at 4° C. Alternatively, the blood may be separated into its components, such as cellular constituents, red and white cells, platelets, and proteins, such as albumin and globulins including antihemophilic and other clotting factors, and processed automatically for frozen, long-term storage, utilizing a disposable module specifically designed for this purpose in combination with appropriate hardware, though not necessarily the same apparatus as is used for the controlled withdrawal and infusion.

On occasion, in the processing of fluid, it is necessary to control the pressure at a specific valve or through a sequence of values in accordance with the preset program. Pump $P_1$ (FIG. 1) in combination with control valve $V_2$ can be used to provide the required pressure in the fluid processing portion of the apparatus.

Another example of fluid processing is the previously-disclosed use of controlled blood pressure in a hemodialysis system to produce and control, in part, the rate of water and solute transfer across the dialysis membrane; or, as noted in U.S. Pat. No. 3,616,926, where the membrane support system is ". . . , modified to operate for filtration (of blood) instead of dialysis. The membrane clearing capacity of laminar flow skimming can be augmented by providing for either pulsatile flow or alternate synchronized internal pumping" (column 3, line 42, and following).

A most important feature of the invention which is indicated only symbolically in FIGS. 1 and 2 is that S1, as discussed previously, may actually comprise several sensors or sensor systems which serve to monitor the physiologic status of the patient. These are specified as to function by the combination of the interface design, providing the physiologically compatible functional attachment to the patient, whether via a disposable component (such as a catheter) or by direct connections (as with electrodes), in combination with the logic system and programming of the microcomputer. The system, as described in part previously, and as will be detailed below, easily adapts a general purpose sensor, such as physiologic pressure sensor with a potential range from −100 to +350 mm Hg to monitor diverse pressures such as arterial blood pressure and venous blood pressure, pulmonary capillary wedge pressure, hemodialysis fistula access pressure or extracorporeal blood circuit pressure, by providing the necessary interface to the patient and a matching program for specifying the meaning of the sensor output. Other sensor systems easily adapted to this apparatus include plethysmographs, electrocardiograph, oximeters, substance-specific electrodes or possibly even more complex devices such as mass-spectrograph systems.

A basic advantage to this system is the wide variety of treatments made available by design of the module used. Thus, there are various types of treatments suitable for replacement of all or part of the patient's normal kidney function, including for example, perfusion of a column of activated charcoal or other sorbent, perfusion of ion-exchange or specific compound-binding resin columns and enzymatic and chemical reaction systems, using whole blood or filtrate, returning all or a portion of the blood and/or filtrate to the patient with or without controlled addition of additional treatment materials prior to reinfusion.

A crucial variable in the (ultra) filtration process is the pressure difference across the membrane 46. Pressure is built up by pump P1 and the necessary resistance to flow is provided largely by valve V2. Control of valve V2 is effected by controller C2, as shown in FIG. 1. With a suitable membrane and support system, capable of withstanding the pressure necessary to produce filtration, the filtrate will collect in compartment 44, FIG. 3, and can be pumped by pump P3 to additional processing. Pump P3, therefore, under control by MC is similar to and synchronized with pump P1 (not shown for clarity in the schematic) and can generate negative pressure on the filtrate side of the membrane to augment the pressure gradient and effectiveness of filtration. In this configuration, flow meter FM2 is disposed in line 47 for return of blood to the patient, and flow meter FM1 is disposed in line 11 as also shown in FIG. 1. Each is joined to integrator means I2 and I1, respectively, which may in fact be sub-routine programming of the microcomputer MC using analogue flow meter outputs after conversion in the A/D component of the electronic information processing portion of the apparatus. The output from the A/D component is then input for calculation of these flow rates in digital form suitable for subsequent use as input for control of programming subroutines. The rate of filtration can be determined from the difference between the instantaneous reading of FM1 and FM2, or from the volume from subtraction of the value of I2 from I1 as a function of time.

As noted previously (U.S. Pat. No. 3,946,731 and this application) saline, or other therapeutic infusions can be added to the fluid or blood returning to the patient, as for example if the output of sensor S1 indicates that the patient's requirement for increased blood volume to counteract the effects of too rapid removal of blood as evidenced by pressure drop combined with blood withdrawal without blood return. Another example is the dilution of blood prior to filtration to facilitate hemofiltration.

Alternatively, the output or a portion of the output of regeneration unit 56 or other treatment devices such as those mentioned previously, can be directed via vessel 32 and valve V3, under control of controller C1 back to the patient, or to the treatment section.

Should manual control be used, the MC output would activate the display means 12, to indicate the necessary manual adjustment to any or all of the involved functional subsystems. The display means can also be used to indicate the status of automatically controlled variables.

Alternative filtration sensing mechanisms have been described in '731 and its divisional application Ser. No. 625,738. As is evident, it is not necessary to utilize all the integrator means shown, and various combinations of these sensing and control systems can be used to obtain similar results. It is, however, convenient to balance the economics of function against the required degree of control and safety and to utilize redundant sensing and control capabilities to provide both independent safety monitoring and adaptability of the apparatus to various functions through the use of modular interface components, as described previously by adaptation of individual sections or subsystems for a variety of purposes. Where there is redundant hardware capability necessitated by the anticipated extended function design, these functions may be utilized for the additional safety of effectiveness they lend to a procedure.

As an example of adaptability, pump P3 of FIG. 3 can serve a double purpose, in the use of the system for hemodialysis, in making possible the reduction of the size of the apparatus. This pump functions in the control of the pressure in compartment 44, including reduction below atmosphere pressure. The second function of pump P3 is to establish a desired pressure in the filtrate treatment of fluid regeneration unit 56.

The dialysate circuit portion of the system when set up for hemodialysis may include monitoring and control functions which extend its usefulness. Thus, water (in the form of dilute solution) recovered in fluid regeneration unit 56 of FIG. 3 may be used for preparation of saline for infusion or for preparation of dialysate by controlled mixing with appropriate concentrates, the preparation being carried out by continuous control addition or by premeasuring in one or more reservoirs. This type of multiple use has already been disclosed in my U.S. Pat. No. 3,774,762, but the present system is an improvement over that disclosed in said Patent in that the flexibility and adaptability to a variety of procedures is much greater. In addition, discrete portions of the apparatus shown in my earlier Patent and constructed as taught herein can advantageously be constructed and used where the full range of flexibility is unnecessary or uneconomical.

Figure 10:
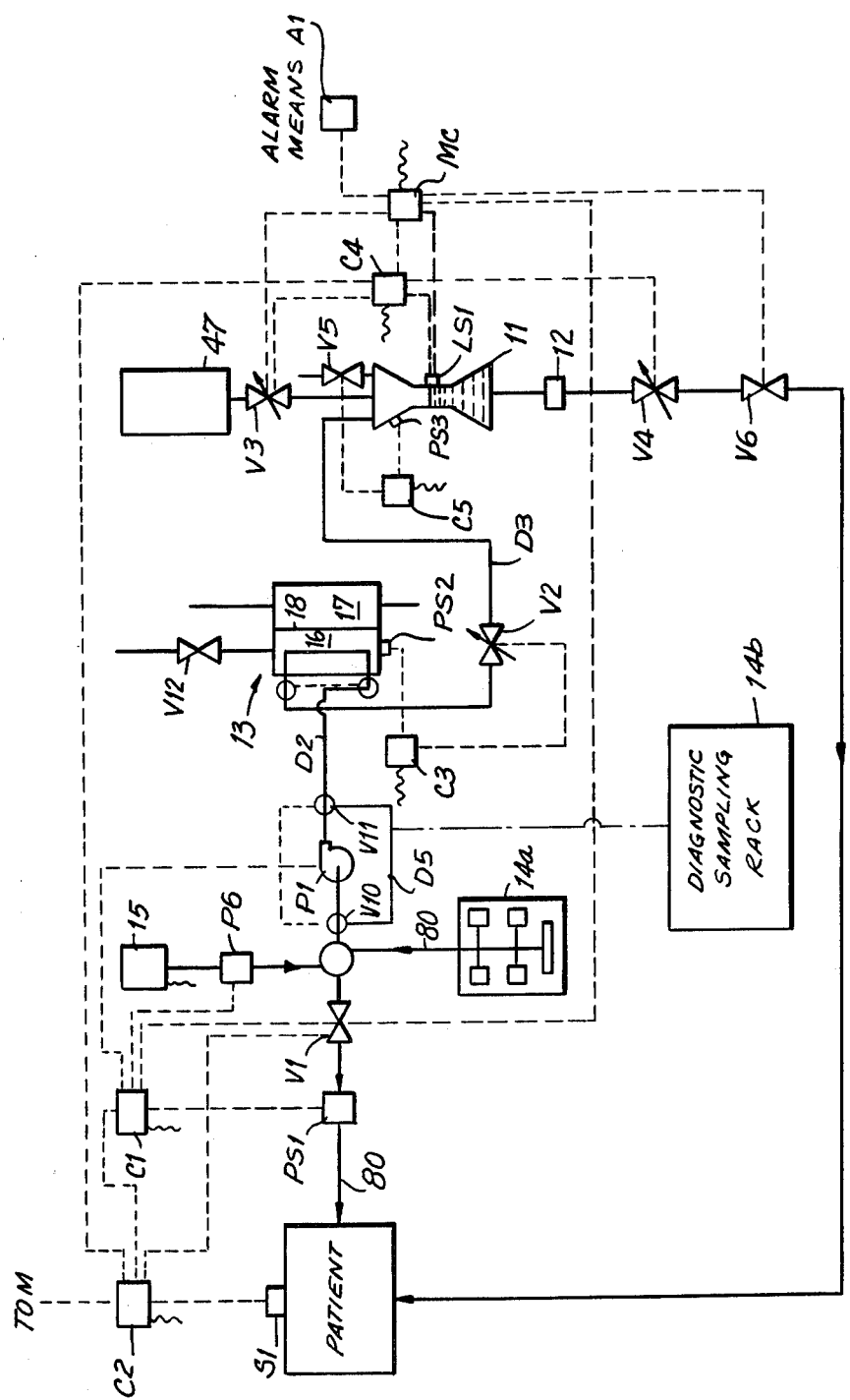
FIG. 10 is an embodiment for extracorporeal circulation of fluid including hemodialysis, for withdrawal of fluid and for medication by infusion of fluid.

As is evident from the embodiments of the invention described above, the precise connections require depend upon the particular procedure to be carried out, and the connections involved include the number of access lines to the patient's vasculature. FIG. 10 shows a two-line unit suitable for monitoring arterial pressure and for providing a controlled venous infusion, with or without pressure-monitoring simultaneously. Pump P6 provides a heparin-infusion "keep open" flow to the arterial pressure monitoring line D1. The "treatment" pack connected through medication input line 80 is a source of infusion fluids, such a system being particularly useful for monitoring a patient in shock or after surgery. With appropriate fluids and medication, the programming can be arranged to monitor the ECG and automatically treat arrhythmias as well as hypotension.

Further, with respect to FIG. 10, IV fluid may be supplied from reservoir 15 by gravity or by means of pump P6 to duct D1. Prescription pack 14A under the control of the microcomputer adds medication as needed to the saline from reservoir 14.

Where pump P1 is operated in the normal direction, fluid taken from the patient can be diverted through valve $V_{10}$ to diagnostic sampling pack 14b. The remainder of the apparatus shown schematically in FIG. 10 is as described in my U.S. Pat. No. 3,946,731 incorporated herein by reference.

Figure 11:
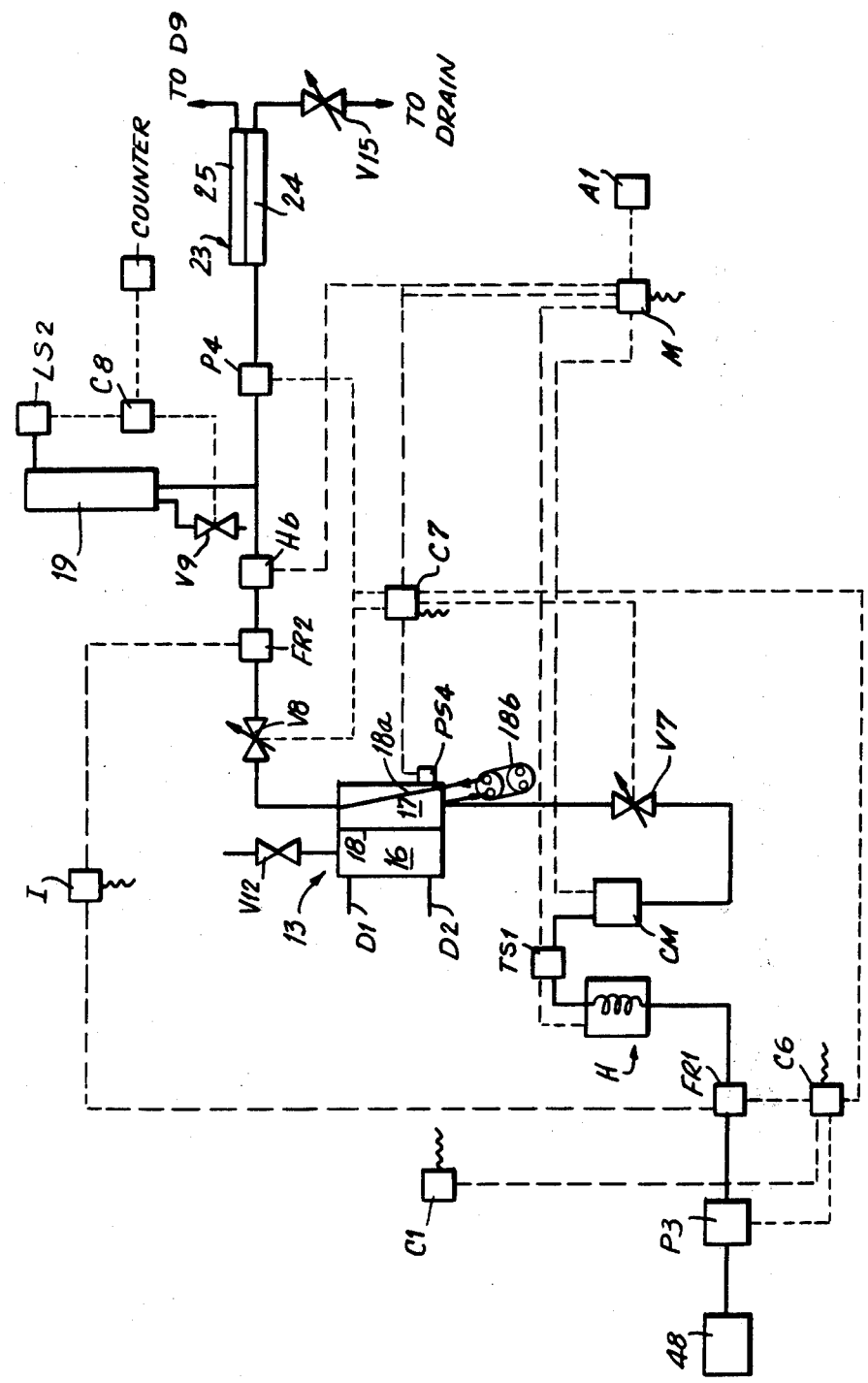
FIG. 11 is an embodiment for circulation of fluid using a catheter for determining the physiological status of the patient.

FIG. 11 also from my U.S. Pat. No. 3,946,731 except for added catheter connection 18a to catheter 18b illustrates the utility of the dialysate control portion of the system in monitoring hypotension or shock.

With the danger of contamination eliminated by the combination of a modular disposable unit with hardware, the ultrafiltration control system can be used for precise bladder irrigation to reduce the incidence of infection, while measuring urine output, a parameter for estimating renal blood flow; the knowledge of this parameter is useful in monitoring tissue perfusion in a patient with shock, whatever the etiology, whether volume depletion due to hemorrhage or dehydration, cardiogenic shock with reduced cardiac output, or due to loss of peripheral vascular tone and intravascular blood pooling as in bacteremia with endotoxin shock.

This has been shown in the schematic FIG. 11. Irrigation fluid from reservoir 48 can be pumped under precise control through heater H to a catheter in a patient's bladder, with substitution of a double lumen catheter in the disposable modular unit with connections to the dialysate side of the hemodialysis system, including pressure sensor PS4. This allows safe, constant temperature and pressure perfusion of the patient's bladder, while outflow monitoring similar to that of the ultrafiltration control system will permit discrimination of the additional outflow volume resulting from urine production.

A high degree of safety in the operation of the apparatus accrues not only from the fail-safe features, but from the fact that a module can be coded so that it can be used with a matching program. Thus, in FIG. 12A, module 149 is shown as having imprinted thereon or otherwise associated therewith a coding strip 151 which may be of the optical or magnetic types, such coding being now widely available and the interface being constructed to read the coding. The strip can be coded to match a specific program or procedure and the MC can be constructed or programmed to generate a signal should the module and the program inserted into the MC not correspond. In another coding embodiment, a pocket or recess 153 in module 152 can accept a tape or disc 154 similarly coded.

The structure of the flexible portion of a module 156 which cooperates with the roller pump of FIG. 4 is shown in FIG. 13. In this construction, flexible tubing 158 fits into recess 64 in interface 62. Sheet 157 is formed to fit over tubing 158 and holds it against the interface. Opening 159 in sheet 157 provides for access of the pump rollers to the tubing.

An arrangement for continuous hemofiltration and for plasmapheresis is shown schematically in FIG. 14 in which a canister has a membrane 162 of a porosity appropriate to the procedure to be carried out and which divides the canister into a blood chamber 164 and a filtrate chamber 167. Blood taken from a patient along duct 163 reaches blood chamber 166 after treatment and is returned to the patient through duct 166. The filtrate is transferred to canister 168 for ultrafiltration to recover the ultrafiltered water containing some salt and other solubles. The ultrafiltrate is returned to the input line 163 through duct 169. To avoid excess dilution, concentrate containing replacement ionic material and/or proteins is added from reservoir 171. Where plasmapheresis is to be carried out, filtrate from canister 168 is taken through duct 170 to chamber 173, from which recovered product may be taken along duct 174 to be returned to the patient.

A particularly suitable pressure transducer for use with modules is shown in FIG. 15 in which transducer 176 is covered with a flexible diaphragm 177, the deflection thereof under applied pressure being measured either electrically as by wire 178 or hydrostatically through the transducer itself. The outer face of diaphragm 177 is brought into contact with fluid or gas in tube 179 of module 181. The diaphragm may be permanently emplaced on the transducer, but it is sufficiently exposed so that it can be readily sterilized. Preferably, it should be replaced for each use.

These highly adaptable, stand-alone, units suitable for intensive care unit (ICU) medical procedures such as hemodialysis, monitoring and treatment in Cardiac Care Units (CCU), burn units and recovery rooms as well as for use on general medical and surgical floors, can form an integral part of a computer based Hopsital system. At a basic level, units within a particular area can be tied together for a single patient for for multiple patients and to a central monitoring station to provide remote data access and record keeping functions. The necessity and advantages of this are apparent, as an improvement over standard remote mounting procedures in present intensive care units. The unique aspects of the proposed system are the provision for extension of these capabilities to greater numbers of patients to improve care at all levels of intensity while simultaneously reducing overall costs for care through reduction in the frequency of necessary personnel intervention for prespecified procedures, including routine activities such as 24 hour IV and drug infusions on general medical and surgical floors, as well as sophisticated intensive care.

To fully develop this advantage, however, there can either be provision for hardware interconnection within the Hospital's construction, or some means of telemetry, such as short range carrier frequency radio. The stand-alone capability of each patient unit, with inclusion of the circuitry necessary for coded two-way interrogation simply by plugging into the electrical wiring of a limited geographic area, such as a hospital and its immediate surroundings, would allow inexpensive development of suitable information networks. The obvious extension of this would be to utilize the same system for information transmission throughout the Hospital, and via telephone coupled relay or other information transmission systems to suitably equipped outside offices. Within the Hospital, this system can, of course, be extended to include manipulation of information for non-medical funtions.

It should be noted that the module can, of course, be constructed so as to be reusable, after appropriate cleaning, sterilization and preparation, but for convenience a disposable module seems preferable. Also, it is desirable that the module be manufactured in standardized configurations for reasons of economy, convenience, and to facilitate high levels of quality control.

Controlled infusions of multiple drugs or active agents to provide balanced effects can be carried out by means of the apparatus and appropriate modules. Such effects can be obtained by antagonistic hormone infusions, insulin/glucagon, PTH/calcitonin, or complementary infusions such as FSH/LH, the former pair in response to sensed glucose or calcium concentrations respectively or the latter pair in programmed sequences to stimulate responsive organ functions, including infusions for dynamic diagnostic purposes, to allow complex studies of physiology, such as the hormonal control of the process of ovulation, by the interrelations between gonadotropin-releasing hormone (GNRH), FSH, LH and estrogens.

The system can be used for any dynamic control process with effector and effect, i.e., drug infusion or cardiac output by thermodilution, particularly in view of the fact that a given sensor may be used for a variety of measurements depending on the way in which the program utilizes the signal therefrom. Thus, the microcomputer and the program specify the significance of the signal from the sensor. One such application, the administration of thyrotropin releasing hormone (TRH) to stimulate pituitary release of thyroid stimulating hormone (TSH), utilizes a disposable module in combination with the microinfusion pump to inject the TRH, and periodically withdraw the timed blood samples (with appropriate concentration of anticoagulant), pumping each blood sample into reservoirs via access flow paths controlled by valves (FIG. 4).

This system can, of course, be utilized alone, or in combination with the other subsystems, each of which can be modularized, and constructed as free-standing single purpose units, without violating the basic concept and design of the overall system.

SYSTEM PROGRAMMING—DATA STORAGE

Control of the various procedures, and, particularly, where more than one procedure must be carried out simultaneously, requires a careful approach to the design of the appropriate data storage devices associated with the microcomputer. The amount of data storage for programming of the variety, size and complexity required for the procedure applications, suggests the necessity for resident programming in the MC memory to institute functions of the system and read and activate secondary programming associated with and matching the application requirements of a particular disposable module, and its construction. This secondary programming should, therefore, be keyed to the disposable module to prevent inappropriate matching of disposable module and program. The devices and media for these programs storage systems can be standard units, such as PROM and RAM devices, or magnetic peripheral systems such as those that utilize media such as magnetic tape, disc or card storage of information. These systems may be part of the hardware disposable integration, such as a magnetic strip on the disposable module and/or inserted into the disposable module prior to use or as a separate component. The memory medium would be "read" by the matching hardware components and used for data storage during programmed operation, as required.

Similarly, the read-out device previously specified may be any standard system, or combination of systems, such as CRT displays, meters, LED or LCD display and hard copy printers. The inclusion of a hard copy printer and input keyboard makes possible a directly visible record of the input specifications given to set or modify the device's internal programming or functions, and the patient's status during a procedure, in addition to long term storage of data on the magnetic or other computer media.

There are several further advantages to the system outlined, utilizing the information processing, input and read-out capabilities of this bedside system. First, inclusion of telemetry or remote I/O capabilities in the electronics portion, such as standard modems, parallel line interface, or other data transmission modalities, allows construction of an information processing network including, in addition to the remote terminal monitoring of a procedure discussed previously, administrative inventory and accounting controls, and remote input of data, such as clinical laboratory assay results or other specific service reports. These inputs may be data essential to the procedure in progress or simply part of the remainder of the record of the patient's care, providing an automatic, bedside record-keeping system to simplify the flow of information within the Hospital, and its function as a whole, including, with provision for external electronic access telemetry and terminal systems, outside monitoring and control when desirable, physicians' offices, for example.

One example of such a system, designed to avoid the necessity of complex rewiring in a Hospital, includes carrier current limited range radio telemetry for data transmission via the existing electrical power circuitry within the Hospital and/or in a Hospital and its surrounding community, and accessed via tuned radio broadcast and receiver circuitry with appropriate decoding.

Modular Disposable Component Construction

As shown in the aforenoted patents, the apparatus consists of a group of controllers and sensors fixed in position within hardware, with active access and function points specified by design. The concept of the access door is modified herein. These points of function are anticipated, and matched by the "active principles of the procedure in a spatially ordered configuration" within a module specifically designed to integrate with the hardware.

The exact construction of the "disposable component", or module, originally shown in U.S. Pat. No. 3,774,762, beginning at column 6, line 8, as being constructed of plastic sheets for reasons of economy, is obviously not the critical parameter, as discussed subsequently in U.S. Pat. Nos. 3,912,455 and 3,946,731, showing multiples of sheets and/or flexible tubing, U.S. Pat. No. 3,946,731, column 3, line 18, column 12, line 38, and column 13, line 55, for example.

It should be, therefore, obvious that the grooved walls surrounding the tubing or flow paths in essence form a rigid, at least partially enclosing structure supporting the spatial organization of flow paths and fixing the points of interaction with the sensors and controllers in hardware, and that once integrated, the only portions of the apparatus that remain flexible, or require flexibility for operation or function are certain interaction points, such as pressure sensor contacts of these which cooperate with pumps. Moreover, inlet and outlet of fluid from hardware to disposable and the reverse, as specified above, is also possible, if necessary, without violating the basic concept of the functional relationship between hardware and disposable.

It should be equally obvious that (1) the use of tubing, rigit or semi-rigid structures, constructed with flexible or other specialized hardware interface points in a predetermined spatial organization, are simply more extensive modifications of the basic system and structure. (2) The plastic sheet or tubing structure provides the necessary connections between points of function and a lining for the rigid support system, again, an inexpensive way of providing a bio-compatible interface between fluids, blood and the extra-corporeal circulation equipment. (3) The structure, therefore, of the modular disposable component could, obviously, be constructed of, for example, molded plastic with a system of functional-interface seals and locks to facilitate integration with the appropriate hardware sensors and controllers. (4) Any of these constructions can, with appropriate treatment, be prepared for reuse. This might be necessary, with the added expense of some constructions, but certainly does not significantly change the basic concept of the apparatus or its function. (5) There are various combinations of construction possible, with tubing sheet, semi-rigid, rigid, disposable and reusable portions, without changing the basic concept of the apparatus or its function. (6) Finally, it is obviously possible to stack these structures for a procedure as a single functional disposable unit in a multilayer sandwich construction, with or without access between layers and to both sides and/or inner layers from hardware.

Considering the system as a whole, therefore, the apparatus consists of a group of controllers and sensors in a preselected position associated with an interface, with active access and function points specified by design. These points of function match associated regions in a variety of modules for carrying out procedures under the monitoring of a microcomputer, either automatically by the microcomputer or by an attendant under the instruction of the computer. Sensors may be moved to different points of function.

As can be seen, then, the interface of the apparatus for cooperating with a module provides a number of useful patterns of flow through the module, the interface, in a preferred form, having grooved walls which surround or partially surround, or attach to disposable pressure sensor transducer tubing or flexible ducts for controlling the flow therethrough. The only portions of the apparatus which remain flexible, or require flexibility for operation or function, are certain interaction points such as pressure sensor contacts or pumps. The module may be constructed for tubing and may include rigid or semi-rigid structures with flexible portions or otherwise specialized hardware-interface points in a predetermined spatial organization. (including linear) The plastic sheet or tubing structure provides interconnection for the modular support systems, the pattern of the module providing for transfer of fluid between portions of the system, the system and a patient. The module could be constructed, for example, of molded plastic with a system of functional interface seals and locks to facilitate integration with the appropriate hardware sensors and controllers. It should also be noted that should the module be constructed in the form of a multilayer sandwich, access may be provided to both faces of the sandwich from the interface of the apparatus.

It will thus be seen that the objects set forth above among those made apparent from the preceding description, are efficiently attained and, since certain changes may be made in carrying out the above method and in the construction set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention which, as a matter of language, might be said to fall therebetween.

What is claimed is:

1. Modular vessel structure, hereinafter termed "module", arranged and constructed for carrying out a specific medical procedure in cooperation with an apparatus for use with said apparatus which includes fluid-transfer means, sensor and signalling means, valve means and computer means programmable for carrying out a plurality of medical procedures including said specific medical procedure, and indicator means for indicating appropriate adjustment to be made in said procedure, the term "medical procedure" being taken to include therapeutic and diagnostic procedures, said sensor means being arranged and constructed for sensing a variable relevant to a fluid within said module and relevant to the progress of said procedure, said signalling means connecting said sensor means with said computer means for communicating the value of said property thereto, said module comprising:

a plurality of conduit means arranged in a pattern for cooperation with said apparatus, a sufficient portion of at least one conduit means being arranged and constructed to be accessible for cooperating with said fluid-transfer means for transfer of fluid therethrough at a controlled rate, and at least one portion of at least one conduit means being arranged and constructed to be accessible to said sensor and signalling means for the said sensing of said property, said module including designation means for indicating to said apparatus and thereby to said computer means the procedure for which said module is designed, thereby enabling said computer means to establish whether there is correspondence between said module and a selected program.

2. The module as defined in claim 1, wherein said conduit means comprises flexible tubing.

3. The module as defined in claim 2, wherein said base layer comprises a second sheet, at least a portion of said second sheet being flexible for cooperating with said fluid-transfer means and said sensor means.

4. The module as defined in claim 2, wherein said module includes semi-permeable membrane means of a permeability suitable for filtration, said one conduit means being arranged and constructed for connecting with a patient for taking blood therefrom and for conducting said blood to one face of said membrane means, said module further comprising second conduit means for returning said blood from said one face to said patient, and further comprising reservoir means for storage of a solution of essential solute in water, third conduit means for transfer of said solution to said one face, and fourth conduit means for transfer of filtrate away from the other face of said membrane means.

5. The module as defined in claim 1, wherein said conduit means comprises at least a portion of a first sheet and a base layer, said first sheet being sealed to said base layer, said first sheet portion being flexible for cooperating with said fluid-transfer means and said sensor means.

6. The module as defined in claim 1, wherein said module comprises frame means for holding said plurality of conduit means in said pattern.

7. The module as defined in claim 1, wherein said module comprises program means for programming said computer means for carrying out a selected procedure.

8. The module as defined in claim 1, wherein said module comprises a gas-permeable membrane.

9. The module as defined in claim 1, wherein said module includes membrane means of a permeability suitable for separation of blood cells from high molecular weight solutes in blood as well as from ions and water, and for thereby producing a retained fraction and a permeate fraction, said one conduit means being arranged and constructed for connecting with a patient for taking blood therefrom and for conducting said blood to one face of said membrane means, said module further comprising second conduit means for returning blood and said retained fraction from said one face to said patient, and third conduit means for conducting said permeate fraction away from the other face of said membrane means.

10. The module as defined in claim 9, wherein said module includes fractionation means for separating said permeate into fractions, and fourth conduit means for selectively returning a fraction to said patient, to storage or to further treatment.

11. The module as defined in claim 1, wherein said module includes first conduit means connectable with an individual for taking body fluid therefrom and reservoir means for receiving body fluid from said first conduit means.

12. The module as defined in claim 11, further comprising second conduit means for receiving body fluid from said reservoir means, said second conduit means being connectable with said individual for returning said body fluid to said patient.

13. The module as defined in claim 11, further comprising reagent means in said reservoir means for reacting with said body fluid.

* * * * *